US006723702B2

(12) United States Patent
Conrad et al.

(10) Patent No.: US 6,723,702 B2
(45) Date of Patent: Apr. 20, 2004

(54) USE OF RELAXIN TREAT DISEASES RELATED TO VASOCONSTRICTION

(75) Inventors: Kirk P. Conrad, Cranberry Township, PA (US); Martyn Lewis, Menlo Park, CA (US); Elaine N. Unemori, Oakland, CA (US); Xinfan Huang, Menlo Park, CA (US); Carol A. Tozzi, Jackson, NJ (US)

(73) Assignees: RAS Medical, Inc., San Mateo, CA (US); The University of Medicine and Dentistry of New Jersey - Robert Wood Johnson Medical School, New Brunswick, NJ (US); The University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/780,752

(22) Filed: Feb. 9, 2001

(65) Prior Publication Data

US 2002/0019349 A1 Feb. 14, 2002

Related U.S. Application Data

(60) Provisional application No. 60/181,408, filed on Feb. 9, 2000, provisional application No. 60/200,284, filed on Apr. 28, 2000, and provisional application No. 60/242,216, filed on Oct. 20, 2000.

(51) Int. Cl.$^7$ .......................... A61K 38/00; C07K 14/64
(52) U.S. Cl. .............................. 514/12; 514/2; 530/303; 424/198.1; 604/19
(58) Field of Search ....................... 514/2, 12; 530/303; 424/198.1; 604/19

(56) References Cited

U.S. PATENT DOCUMENTS

| | | | |
|---|---|---|---|
| 4,624,804 A | | 11/1986 | Voelter et al. |
| 5,166,191 A | | 11/1992 | Cronin et al. |
| 5,451,572 A | * | 9/1995 | Cipolla et al. ................. 514/21 |
| 5,952,296 A | * | 9/1999 | Bigazzi ......................... 514/3 |
| 6,211,147 B1 | * | 4/2001 | Unemori ........................ 514/2 |

FOREIGN PATENT DOCUMENTS

WO    WO 95/07711    3/1995

OTHER PUBLICATIONS

Danielson, L. A. et al. (1999) Relaxin is a potent renal vasodilator in conscious rats. J Clin Invest. vol. 103, pp. 525–533.*

Danielson L. A. et al. (Sep. 1998) J. Am. Society of Nephrology, vol. 9, p. 336A, Abstract No. A1707.*

Ahokas, R. A. et al. (1989) Lack of evidence of a vasodepressor role for relaxin in spontaneously hypertensive and normotensive pregnant rats. Am. J. Obstet. Gynecol. vol. 161, pp. 618–622.*

Charney et al. (1993) "The role of the coronary collateral circulation in limiting myocardial ischemia and infarct size." *Am. Heart J.*, vol. 126:937–945.

Harada et al. (1994) "Basic Fibroblast Growth Factor Improves Myocardial Function in Chronically Ischemic Porcine Hearts." *J. Clin. Invest.*, vol. 94:623–630.

Henry (1999) "Therapeutic Angiogenesis" *BMJ*, vol. 318:1536–9.

Lopez et al. (1998) "VEGF administration in chronic myocardial ischemia in pigs." *Cardiovascular Research*, vol. 40:272–281.

Losordo et al. (1998) "Gene Therapy for Myocardial Angiogenesis." *Circulation*, vol. 98:2800–2804.

Patel et al. (1999) "Safety of Direct Myocardial Administration of an Adenovirus Vector Encoding Vascular Endothelial Growth Factor 121." *Human Gene Therapy*, vol. 10:1331–1348.

Unger et al. (1994) "Basic fibroblast growth factor enhances myocardial collateral flow in a canine model." *Am. J. Physiol.*, vol. 266:H1588–1595.

Yang et al. (1998) "Substantially Attenuated Hemodynamic Responses to *Escherichia coli*–Derived Vascular Endothelial Growth Factor Given by Intravenous Infusion Compared with Bolus Injection." *The Journal of Pharmacology and Experimental Therapeutics*, vol. 284(1):103–110.

* cited by examiner

*Primary Examiner*—Karen Cochrane Carlson
*Assistant Examiner*—Samuel W Liu
(74) *Attorney, Agent, or Firm*—Paula A. Borden; Bozicevic, Field & Francis, LLP

(57) ABSTRACT

The invention related to methods of treating disease related to vasoconstriction that is a major factor in hypertensive vascular diseases and vasodilation, generally comprising administering to an individual an effective amount of a pharmaceutically active relaxin. Relaxin functions to increase both vasodilation and angiogenesis in males as well as females, and is useful in treating a wide variety of diseases relating to vasoconstriction.

17 Claims, 15 Drawing Sheets

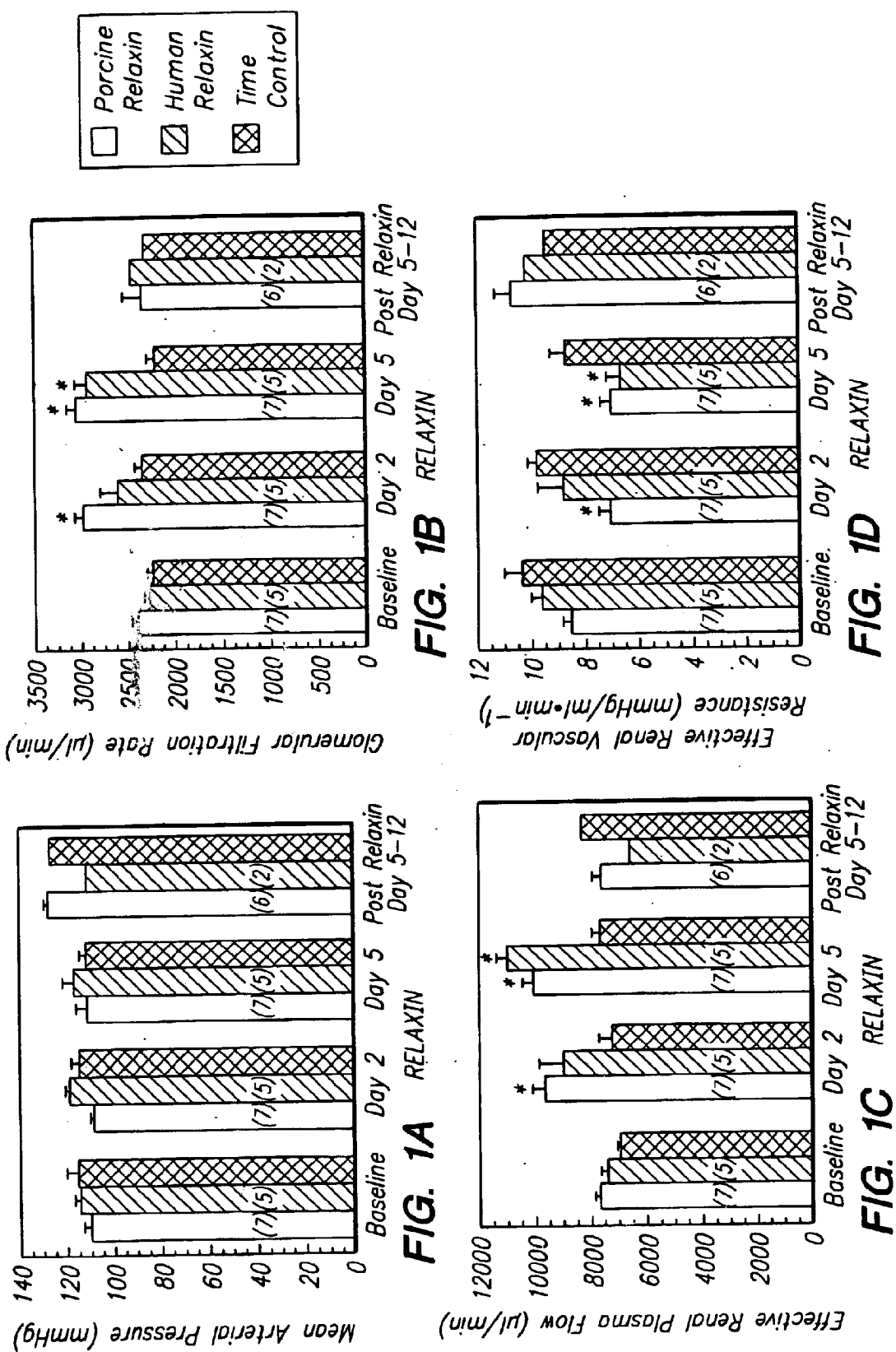

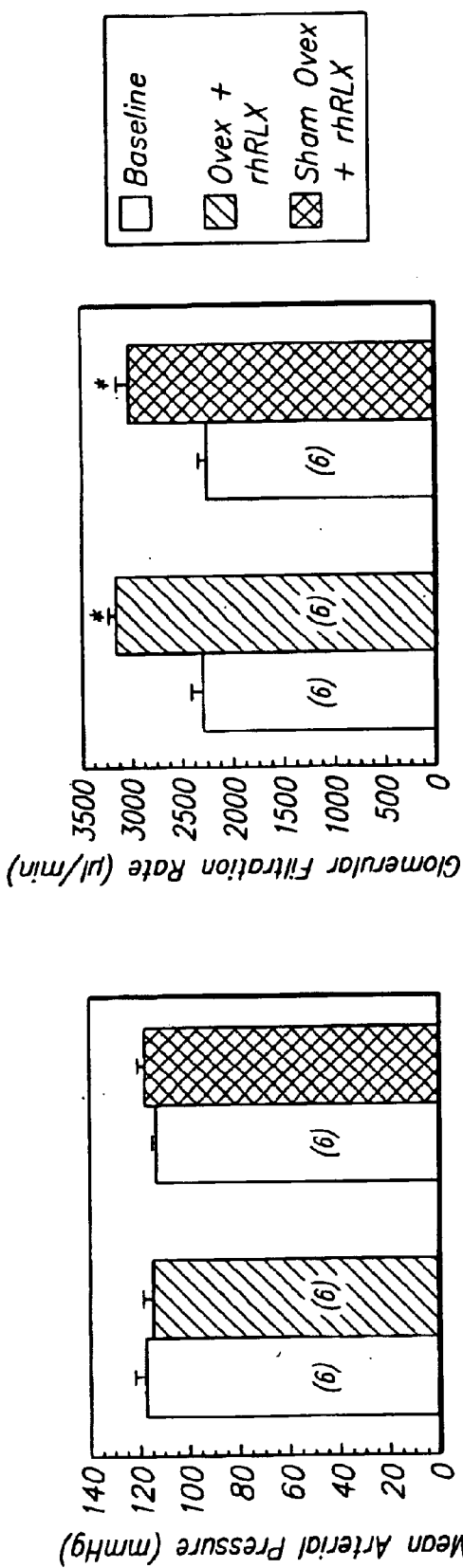
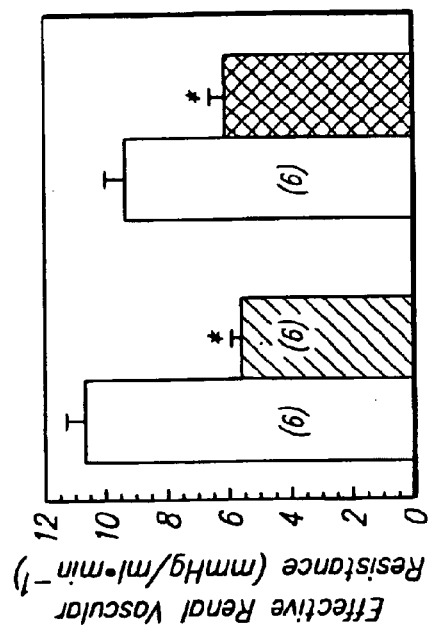
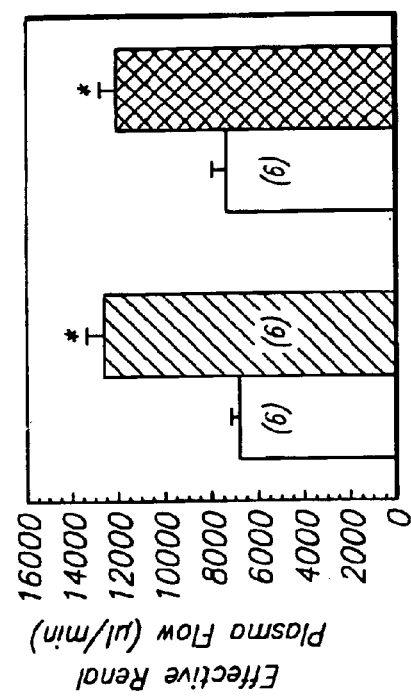
FIG. 2A
FIG. 2B
FIG. 2C
FIG. 2D

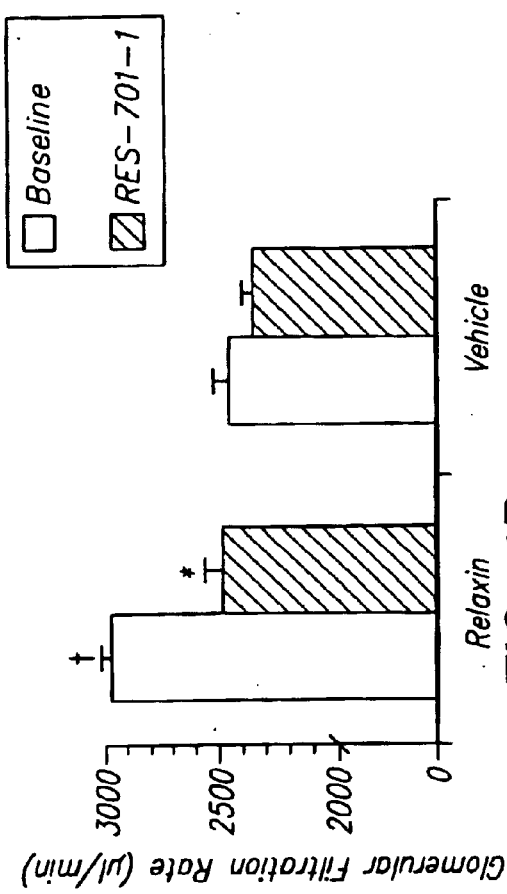
FIG. 4B
FIG. 4A
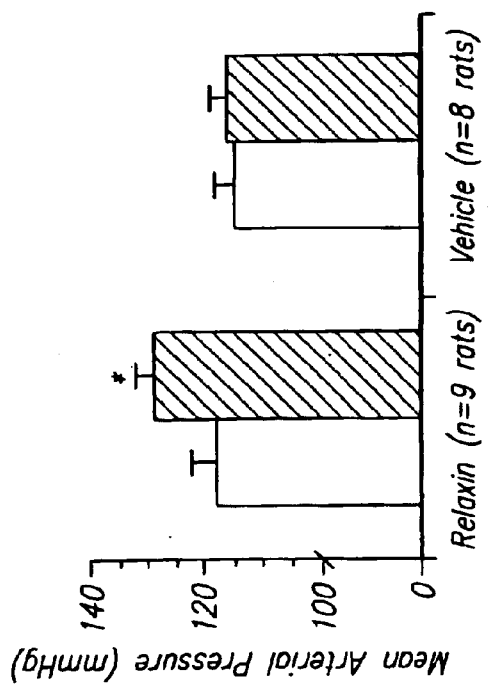
FIG. 4C
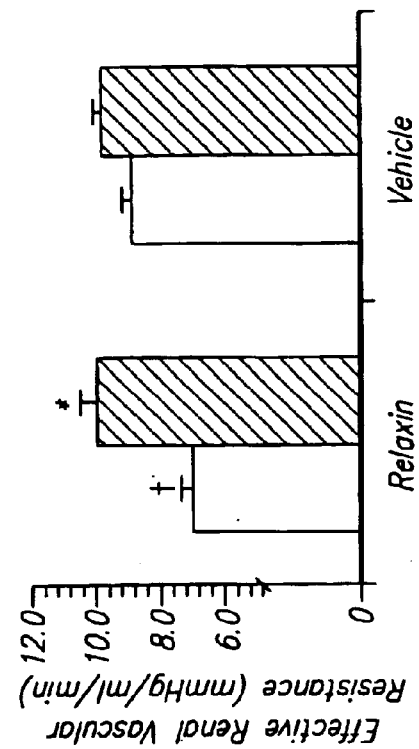
FIG. 4D
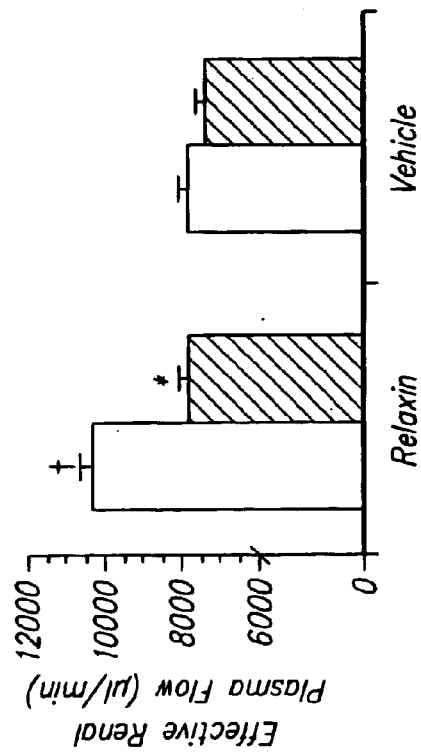

FIGURE 8A
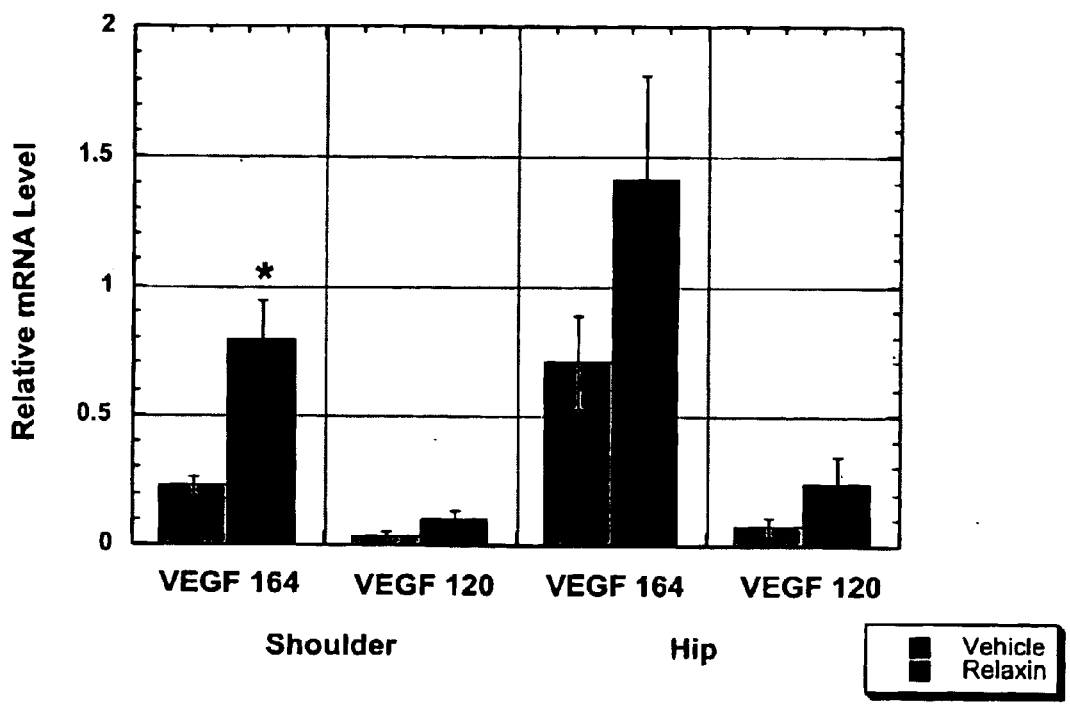
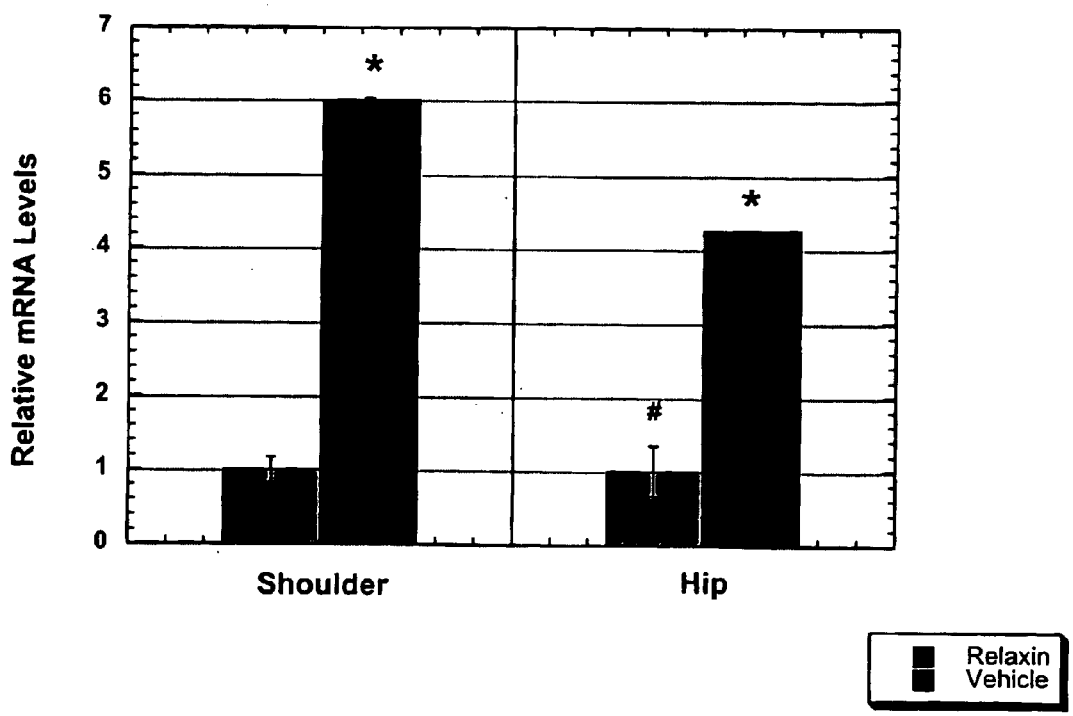
FIGURE 8B

USE OF RELAXIN TREAT DISEASES RELATED TO VASOCONSTRICTION

CROSS-REFERENCE

This application claims the benefit of U.S. provisional patent application Nos. 60/181,408, filed Feb. 9, 2000; 60/200,284, filed Apr. 28, 2000; and 60/242,216, filed Oct. 20, 2000, each of which is incorporated herein by reference in their entirety.

GOVERNMENT RIGHTS

The United States Government may have certain rights in this application pursuant to National Institutes of Health grants RO1 HD30325 and KO4 HD01098.

FIELD OF THE INVENTION

This invention is in the field of diseases related to vasoconstriction, and in particular to the use of relaxin to treat diseases related to vasoconstriction.

BACKGROUND OF THE INVENTION

Vasoconstriction, or the reduction in the cross-sectional area of the lumen of small blood vessels, is a potentially lethal condition arising in a variety of pathologies, and is due either to vasospasm, inadequate vasodilation, thickening of the vessel wall, or the accumulation of flow-restricting materials on the internal wall surfaces or within the wall itself. Vasoconstriction is a major factor in various hypertensive vascular diseases, as well as conditions which result from such diseases, including progressive generalized atherogenesis, myocardial infarct, stroke, hypertension, glaucoma, migraine, ischemia, and diabetes mellitus, among others.

Hypertension produced by renal disease is generally the result of either an alteration in the renal handling of sodium and fluids leading to volume expansion or an alteration in renal secretion of vasoactive materials, resulting in a systemic or local change in arteriolar tone. The main subdivisions of renal hypertension are renovascular hypertension, and renal parenchymal hypertension.

Hypertensive vascular disease is currently treated with drugs such as diuretics; antiadrenergic agents; vasodilators; calcium entry blockers; angiotensin-converting enzyme (ACE) inhibitors; angiotensin receptor antagonists; and growth factors.

The extent of ischemic myocardial injury caused by coronary vessel occlusion may be mitigated by the provision of collateral blood flow to the myocardium and the subendocardial layers of the heart. Charney et al. (1993) *Am. Heart J.* 126:937–945. Currently, therapeutic angiogenesis is designed to promote the development of supplemental collateral vessels as a means of preserving heart function following an ischemic event. Losordo et al. (1998) *Circulation* 98:2800–2804; Patel et al. (1999) *Human Gene Therapy* 10:1331–1348; and Henry (1999) *British Med. J.* 318:1536–1539. Collateral vessel formation and increased blood flow due to new vessel development and vasodilation of both new and pre-existing blood vessels have been shown to preserve certain aspects of heart function. Two agents that have been used in therapeutic angiogenesis in animal models of chronic myocardial ischemia are vascular endothelial cell growth factor (VEGF), which is an angiogenic and vasodilatory growth factor, and the angiogenic protein basic fibroblast growth factor (bFGF). Harada et al. (1994) *J. Clin. Invest.* 94:623–630; Lopez et al. (1998) *Cardiovasc. Res.* 40:272–281 and Unger et al. (1994) *Am. J. Physiol.* 266:H1588–H1595. However, negative consequences, such as hypotension, tachycardia and reduced cardiac output have been observed when VEGF is given to patients. Yang et al. (1998) *J. Pharmacol. Exp. Ther.* 284:103–110.

To minimize the side effect profile of systemic VEGF and FGF administration, current approaches to induce revascularization and reoxygenation have moved toward direct myocardial or pericardial injection of naked DNA for VEGF, or of VEGF or bFGF protein directly. This requires invasive procedures, often involving thoracotomy. A safe, non-toxic, non-invasive method of promoting angiogenic growth factor expression and a subsequent increase in collateral vessel development could have enormous impact.

Relaxin (RLX) is a low molecular weight protein of approximately 6,000 Da belonging to the insulin-growth factor family that circulates during the luteal phase of the menstrual cycle and throughout gestation in women. It is also produced by the prostate in men. RLX is also a pregnancy hormone in rats. In both species, circulating levels derive from the corpus luteum. Relaxin consists of two peptide chains, referred to as A and B, joined by disulfide bonds with an intra-chain disulfide loop in the A-chain in a manner analogous to that of insulin.

In view of the ongoing problems associated with hypertensive vascular disease, it is clear that there is a need in the art for additional means of treating hypertensive vascular disease. The present invention addresses this need and provides related advantages as well.

SUMMARY OF THE INVENTION

The present invention provides methods for treating diseases or disorders related to vasoconstriction, generally comprising administering a formulation comprising a therapeutically effective amount of relaxin. The formulation may be administered by injection, or by sustained-release modes of administration, over a period of time and in amounts which are effective to treat the vasoconstriction-related disease or disorder. Relaxin can act to increase vasodilation, to increase neovascularization (i.e., stimulate, increase, or promote angiogenesis), or both, thereby alleviating the disorder, or symptoms of the disorder. Thus, the invention further provides methods for increasing vasodilation, and methods of stimulating angiogenesis in an individual, generally comprising administering a formulation comprising a pharmaceutically effective amount of pharmaceutically acceptable carrier having therein therapeutically active relaxin.

The invention further provides methods for treating angiotensin-II (AngII)-mediated vasoconstriction. These methods generally comprise administering a formulation comprising an amount of relaxin effective to reverse, inhibit, or reduce the vasoconstricting effects of AngII.

The invention further provides methods for treating endothelin-1 (ET-1)-mediated vasoconstriction. These methods generally comprise administering a formulation comprising an amount of relaxin effective to reverse, inhibit, or reduce the vasoconstricting effects of ET-1. In some embodiments, the methods comprise increasing endothelin type B receptor activation in a cell in a blood vessel by administering relaxin to the individual.

The invention further provides methods for treating an ischemic condition, generally comprising administering a formulation comprising an amount of relaxin effective to stimulate or promote angiogenesis and/or vasodilation, thereby treating the ischemic condition. The methods are useful in treating a variety of ischemic conditions. In some embodiments, methods are provided for treating an ischemic condition which arises as a result of myocardial infarct. In other embodiments, methods are provided for treating an ischemic condition associated with a wound. Thus, the invention further provides methods for promoting wound healing.

The invention further provides methods for stimulating angiogenic and/or vasodilatory cytokine expression generally comprising administering a formulation comprising an amount of relaxin effective to vasodilate blood vessels and/or stimulate or promote angiogenic cytokine production. In some embodiments, the methods provide for stimulating expression of basic fibroblast growth factor (bFGF) and/or vascular endothelial cell growth factor (VEGF). Such methods are useful in treating a wide variety of diseases which can be treated by increasing blood flow at or near the site of disease.

The invention further provides a method of increasing renal vasodilation and hyperfiltration, generally comprising administering a formulation comprising an amount of relaxin. These methods are useful in treating a variety of renal pathologies. Accordingly, the invention further provides methods of treating a renal pathology related to vasoconstriction.

The invention further provides a method of reducing pulmonary hypertension, generally comprising administering a formulation comprising an amount of relaxin.

An advantage of the present invention lies in the fact that the safety profile of relaxin in humans is superior to other agents, such as VEGF and FGF.

A further advantage of the use of relaxin to treat hypertensive vascular diseases is that it is effective in both males and females.

Another object of the invention is a method whereby therapeutically effective amounts of relaxin are repeatedly administered to a patient over a period of time to obtain a beneficial therapeutic result.

Another aspect of the invention is to repeatedly or substantially continuously administer relaxin over a period of time in a manner so as to maintain therapeutic blood levels of relaxin over periods sufficient to obtain therapeutic results.

A feature of the invention is injectable and sustained-release formulations of relaxin which are useful in the method of the invention wherein the formulation comprises a pharmaceutically acceptable carrier and a therapeutically effective amount of relaxin.

These and other objects, advantages, and features of the invention will become apparent to those persons skilled in the art upon reading the details of the invention as more fully described below.

BRIEF DESCRIPTION OF THE DRAWINGS

FIGS. 1A–D depict the effect of long-term infusion of purified porcine RLX, recombinant human relaxin (rhRLX), or vehicle on mean arterial pressure (A), glomerular filtration rate (B), effective renal plasma flow (C), and effective renal vascular resistance (D). The numbers in parentheses depict the number of rats tested. *p<0.05 vs baseline and vehicle.

FIGS. 2A–D depict the effect of 5-day administration of rhRLX to sham ovariectomized and ovariectomized rats: (A) mean arterial pressure, (B) glomerular filtration rate, (C) effective renal plasma flow, and (D) effective renal vascular resistance. The numbers in parentheses depict the number of rats investigated. *p<0.05 vs baseline.

FIGS. 4A–D are graphs depicting the effect of the specific $ET_B$ receptor antagonist, RES-701-1, on MAP (panel A), GFR (B), ERPF (C), and ERVR (D) in rats administered either rhRLX (4 μg/h) or vehicle for 5 days. +p<0.05 relaxin baseline vs vehicle baseline. *p<0.05 RES-701-1 vs baseline.

FIGS. 8A and 8B are graphs depicting the effects of relaxin on VEGF and bFGF mRNA expression in wound cells. FIG. 8A depicts expression of transcripts of the 164-amino acid and 120-amino acid isoforms of VEGF. FIG. 8B depicts the increase in expression of bFGF in wound cells.

DETAILED DESCRIPTION OF THE INVENTION

Figure 3A:
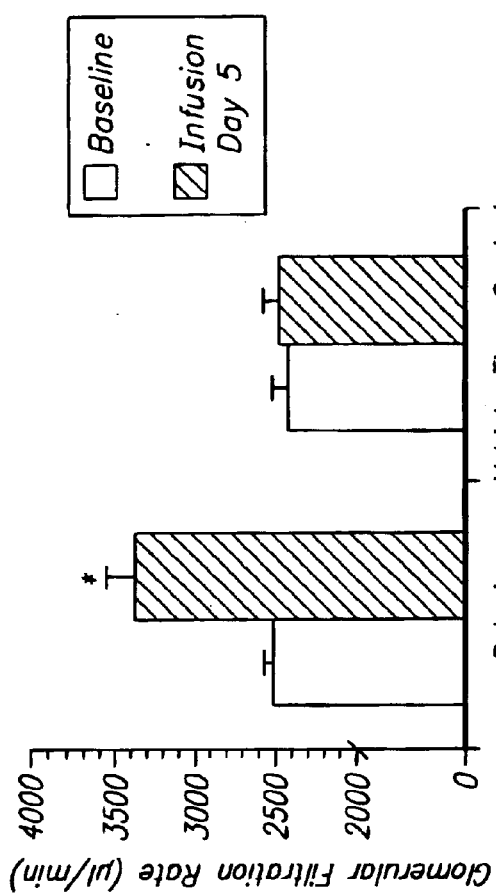
FIGS. 3A–D are graphs depicting the effect of a 5-day infusion of either rhRLX (4 μg/hour) or vehicle (time-control) on mean arterial pressure (MAP) (panel A), glomerular filtration rate (GFR) (B), effective renal plasma flow (ERPF) (C) or renal vascular resistance (ERVR) ERVR (D) in conscious male rats. * p<0.05 vs baseline.
Figure 3B:
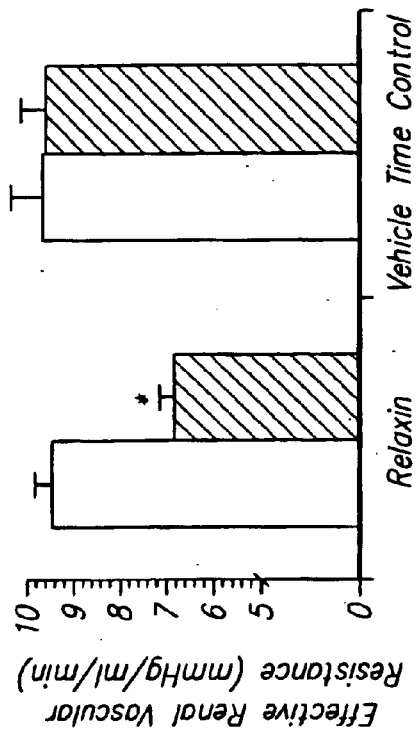
Figure 3C:
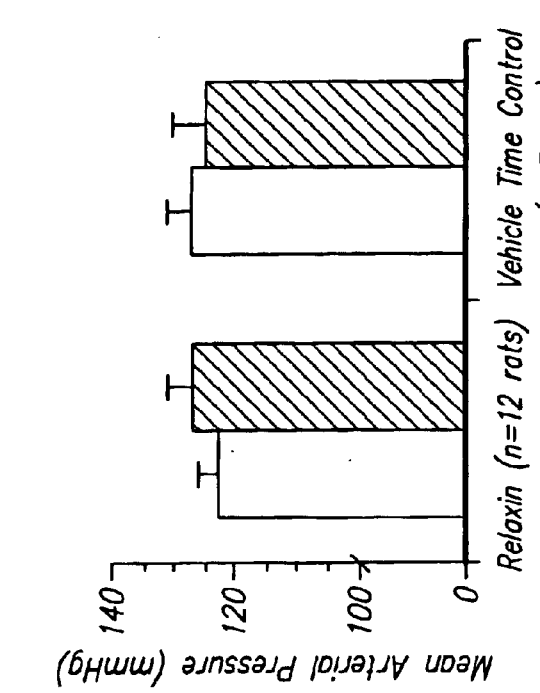
Figure 3D:
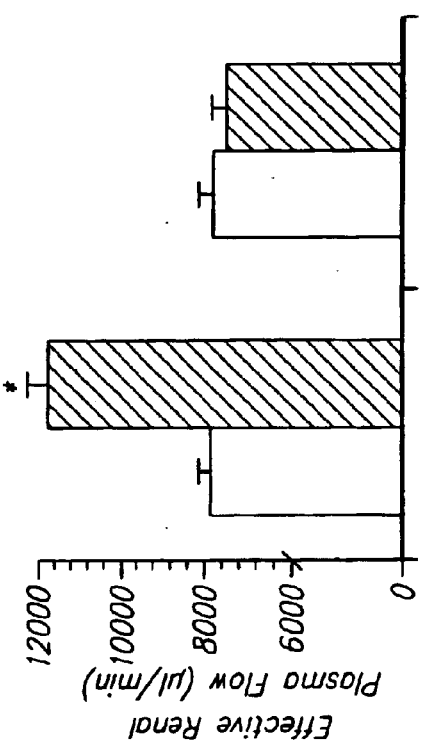

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a disease" includes a plurality of such diseases and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, the terms "disease related to vasoconstriction," "disorder related to vasoconstriction," "disease associated with vasoconstriction," and "disorder associated with vasoconstriction," used interchangeably herein, refer to a disease or condition or disorder that involves vasoconstriction in some manner. The disease may be a disease which is a direct result of vasoconstriction; a disease or condition that is exacerbated by vasoconstriction; and/or a disease or condition that is a sequelae of vasoconstriction. Diseases and disorder related to vasoconstriction include, but are not limited to, pulmonary vasoconstriction and associated diseases and disorders; cerebral vasoconstriction and associated diseases and disorders; peripheral vasoconstriction and associated diseases and disorders; cardiovascular vasoconstriction and associated diseases and disorders; renal vasoconstriction and associated diseases and disorders; and ischemic conditions. Such diseases and disorders include, but are not limited to, chronic stable angina; unstable angina; vasospastic angina; microvascular angina; blood vessel damage due to invasive manipulation, e.g., surgery; blood vessel damage due to ischemia, e.g., ischemia associated with infection, trauma, and graft rejection; ischemia associated with stroke; cerebrovascular ischemia; renal ischemia; pulmonary ischemia; limb ischemia; ischemic cardiomyopathy; myocardial ischemia; reduction in renal function as a result of treatment with a nephrotoxic agent, e.g., cyclosporine A; acute myocardial infarction; ischemic myocardium associated with hypertensive heart disease and impaired coronary vasodilator reserve; subarachnoid hemorrhage with secondary cerebral vasospasm; reversible cerebral vasoconstriction; migraine; disorders relating to uterine vascoconstriction, e.g., preeclampsia of pregnancy, eclampsia, intrauterine growth restriction, inadequate maternal vasodilation during pregnancy; post transplant cardiomyopathy; renovascular ischemia; cerebrovascular ischemia (Transient Ischemic Attack (TIA) and stroke); pulmonary hypertension; renal hypertension; essential hypertension; atheroembolic diseases; renal vein thrombosis; renal artery stenosis; renal vasoconstriction secondary to shock, trauma, or sepsis; liver ischemia, peripheral vascular disease; diabetes mellitus; thromboangiitis obliterans; and burn/thermal injury.

As used herein, the term "relaxin" refers to biologically active (also referred to herein as "pharmaceutically active") relaxin from recombinant or native sources as well as relaxin variants, such as amino acid sequence variants. Naturally occurring biologically active relaxin may be derived from human, murine (i.e., rat or mouse), porcine, or other mammalian sources. The term "relaxin" encompasses human H1 preprorelaxin, prorelaxin, and relaxin; and H2 preprorelaxin, prorelaxin, and relaxin; and recombinant human relaxin. Also encompassed is relaxin modified to increase in vivo half life, e.g., PEGylated relaxin (i.e., relaxin conjugated to a polyethylene glycol), and the like. The term also encompasses relaxin comprising A and B chains having N- and/or C-terminal truncations. In general, in H2 relaxin, the A chain can be varied from A(1–24) to A(10–24) and B chain from B($^-$1–33) to B(10–22); and in H1 relaxin, the A chain can be varied from A(1–24) to A(10–24) and B chain from B(1–32) to B(10–22). Also included within the scope of the term "relaxin" are other insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395. Possible modifications to relaxin amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807. Also encompassed by the term "relaxin" are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this invention so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using the in vitro and in vivo assays mentioned above.

As used herein the terms "isolated" and "substantially purified," used interchangeably herein, when used in the context of "isolated relaxin," refer to a relaxin polypeptide that is in an environment different from that in which the relaxin polypeptide naturally occurs. As used herein, the term "substantially purified" refers to a relaxin polypeptide that is removed from its natural environment and is at least 60% free, preferably 75% free, and most preferably 90% free from other components with which it is naturally associated.

The terms "effective amount" and "therapeutic amount" and the like are used interchangeably here to describe a relaxin formulation that is sufficient to treat a disease related to vasoconstriction. The term "effective amount" means a dosage sufficient to provide treatment for the disease state being treated, i.e., a disease related to vasodilation. In general, an effective amount of relaxin is one that is effective to increase vasodilation and/or to increase neovascularization. The term "increase" is used interchangeably herein with "stimulate" and "promote." The Examples provide general guidance for effective amounts used in rats. Those skilled in the art will readily be able to determine effective amounts for use in human subjects, given the guidance in the Examples. In general, a dose is from about 0.1 to 500 $\mu$g/kg of body weight per day, about 6.0 to 200 $\mu$g/kg, or about 12.0 to 100 $\mu$g/kg. For administration to a 70 kg person, the dosage range would be about 7.0 $\mu$g to 3.5 mg per day, about 42.0 $\mu$g to 2.1 mg per day, or about 84.0 to 700 $\mu$g per day. In some embodiments, for administration to a human, an effective dose is from about 5 $\mu$g/kg body weight/day to about 50 $\mu$g/kg body weight/day, or from about 10 $\mu$g/kg body weight/day to about 25 $\mu$g/kg body weight/day. The amount of relaxin administered will, of course, be dependent on the size, sex and weight of the subject and the severity of the disease or condition, the manner and schedule of administration, the likelihood of recurrence of the disease, and the judgment of the prescribing physician.

The terms "subject" or "individual" or "patient," used interchangeably herein, refer to any subject, particularly a mammalian subject, for whom diagnosis or therapy is desired, particularly humans. Other subjects may include cattle, dogs, cats, guinea pigs, rabbits, rats, mice, horses, and so on. A preferred subject is a human in need of treatment for a disease related to vasoconstriction, particularly a renal disease, and an ischemic condition.

The terms "treatment," "treating," "therapy," and the like are used herein to generally refer to obtaining a desired therapeutic, pharmacologic or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a marnmal, e.g. a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

OVERVIEW OF THE INVENTION

The present invention provides methods of treating diseases related to vasoconstriction, comprising administering to an individual, who has a disease or condition relating to vasoconstriction, an effective amount of relaxin in a pharmaceutical formulation. Relaxin formulations of the invention can act both to increase vasodilation, and to increase formation of new blood vessels. Thus, relaxin can be used to treat a wide variety of conditions related to vasoconstriction. Further, it has been surprisingly found that relaxin, a pregnancy hormone, can function to promote vasodilation and to promote neovascularization in males as well as females. Relaxin can inhibit or reduce angiotensin-II (AngII)-mediated and endothelin-1 (ET-1)-mediated vasoconstriction. It can also promote renal vasodilation and hyperfiltration, which is particularly useful in the context of treating renal disease which result, directly or indirectly, from renal vasoconstriction. It has further been found that relaxin stimulates angiogenic cytokine expression, including bFGF and VEGF, and hence promotes blood vessel formation. It has also been found that relaxin stimulates ischemic wound healing. It has also been found that relaxin is effective in inhibiting progression of pulmonary hypertension. Thus, relaxin's vasodilation- and neovascularization-promoting properties can be used to treat a wide variety of disease conditions arising from vasoconstriction, or inadequate blood supply.

METHODS OF TREATING DISEASES RELATED TO VASOCONSTRICTION

The present invention provides methods for treating diseases related to vasoconstriction. The methods generally comprise administering to an individual in need thereof a pharmaceutical formulation comprising pharmaceutically active relaxin in an amount effective to treat the disease. An effective amount of relaxin is one that is effective to increase, stimulate, or promote, vasodilation; and/or to increase, stimulate, or promote, neovascularization; and/or to promote wound healing; and/or to treat an ischemic condition; and/or to reduce hypertension. The effect of relaxin on vasodilation or neovascularization may be direct or indirect. Modes of administration, amounts of relaxin administered, and relaxin formulations, for use in the methods of the present invention, are discussed below.

An effective amount of relaxin is one that is effective in treating a disease related to vasoconstriction. Whether the disease has been treated is determined by measuring one or more diagnostic parameters indicative of the course of the disease, compared to a suitable control. In the case of an animal experiment, a "suitable control" is an animal not treated with relaxin, or treated with the pharmaceutical formulation without relaxin. In the case of a human subject, a "suitable control" may be the individual before treatment, or may be a human (e.g., an age-matched or similar control) treated with a placebo. Methods for assessing whether a disease related to vasoconstriction has been treated are known in the art, and are described in numerous publications, including, e.g., Young et al., eds. (1996) "Peripheral Vascular Diseases", Mosby-Year Book, Inc. St. Louis, Mo. Additional methods are described hereinbelow.

In some embodiments, the invention provides a method of increasing nitric oxide production in a cell of a blood vessel, comprising administering to an individual a pharmaceutical formulation comprising pharmaceutically active relaxin in an amount effective to increase nitric oxide production in a cell of a blood vessel. Administration of an effective amount of a pharmaceutically active relaxin to an individual in need thereof increases nitric oxide production by at least about 10%, at least about 20%, at least about 30%, at least about 50%, or at least about 75% or more, compared to a suitable control. By administering relaxin to an individual, a cell of a blood vessel in the individual is contacted with relaxin, and nitric oxide production by the cell is increased. A suitable control may be a cell of a blood vessel not contacted with relaxin. Cells of a blood vessel that produce nitric oxide in response to admininstration of relaxin include, but are not limited to, endothelial cells and smooth muscle cells. Methods of measuring nitric oxide production are known in the art; any such method can be used to determine whether nitric oxide production is increased. See, e.g., Gupta et al. (1998) *Hepatol.* 28:926–931; Hill-Kapturczak et al. (1999) *J. Am. Soc. Nephrol.* 10:481–491; Lee et al. (2000) *Microvasc. Res.* 60:269–280; and Berkels et al. (2001) *J. Appl. Physiol.* 90:317–320. Production of nitric oxide by a cell of a blood vessel effects vasodilation, and is thus useful in treating a disease related to vasoconstriction.

In some embodiments, the invention provides methods of treating hypertension, comprising administering to a patient in need thereof a pharmaceutical formulation comprising pharmaceutically active relaxin in an amount effective to reduce hypertension. In some of these embodiments, methods are provided for treating renal hypertension, particularly by increasing renal vasodilation. In other embodiments, methods are provided for treating pulmonary hypertension.

In some embodiments, the invention provides methods for increasing renal vasodilation. Administration of an effective amount of a pharmaceutically active relaxin to an individual in need thereof increases renal vasodilation by at least about 10%, at least about 20%, at least about 30%, at least about 50%, or at least about 75% or more, compared to a suitable control. Parameters of and methods for assessing whether renal vasodilation is increased following relaxin administration are known in the art, including, but not limited to, measuring one or more of the following parameters: effective renal vascular resistance (ERVR); glomerular filtration rate (GFR); mean arterial pressure (MAP); effective renal plasma flow (ERPF); hematocrit; plasma osmolality; and plasma sodium concentration. Administration of relaxin results in one or more of the following: (1) an increase in values for GFR and ERPF; (2) a decrease in ERVR; (3) a decrease in hematocrit; (4) a decrease in plasma osmolality; (5) a decrease in plasma sodium concentration; and (6) a decrease in serum creatinine. A decrease in hematocrit, plasma osmolality, and plasma sodium concentration are indicative of general vasodilation, resulting in an increase in blood volume and a resulting dilution of red cell number and sodium concentration. Methods for measuring these parameters are well known in the art, and are described in Examples 1, 2, and 9.

In some embodiments, methods are provided for treating pulmonary hypertension. Example 5 provides data showing that administration of relaxin, e.g. by infusion over an extended time period, inhibits progression of pulmonary hypertension, as evidenced by an inhibition of collagen deposition in the vessel wall, and by ameliorative effects on compensatory right ventricular hypertrophy. Administration of an effective amount of a pharmaceutically active relaxin to an individual in need thereof reduces pulmonary hypertension by at least about 2%, at least about 5%, at least about 10%, at least about 20%, at least about 30%, at least about 50%, at least about 75% or more, when compared to a suitable control. Whether administration of relaxin reduces pulmonary hypertension can be determined using any method known in the art, including, but not limited to, measuring right ventricular pressure (RVP). Thus, the methods are effective to reduce right ventricular pressure by at least about 2%, at least about 5%, at least about 10%, at least about 20%, at least about 30%, or at least about 50% or more when compared to a suitable control.

In some embodiments, the invention provides methods for increasing or stimulating the expression of angiogenic cytokine production. Administration of an effective amount of a pharmaceutically active relaxin to an individual in need thereof increases angiogenic cytokine production by at least about 10%, at least about 20%, at least about 30%, at least about 50%, at least about 75%, at least about 100% (or two-fold), at least about 2.5-fold, at least about 3-fold, at least about 5-fold, or at least about 10-fold or more, compared to a suitable control. Angiogenic factors include, but are not limited to, FGF, including acidic FGF, basic FGF; VEGF, including VEGF-A, VEGF-B, VEGF-C, and synthetic and recombinant forms which possess VEGF activity, specifically angiogenic activity; hepatocyte growth factor (HGF); platelet-derived growth factor (PDGF); placental growth factor; angiopoietin-1; proliferin; insulin-like growth factor-1; granulocyte colony stimulating factor (G-CSF); transforming growth factor-α; and interleukin-8. Whether angiogenic cytokine production is increased following relaxin administration can be assessed using any method known in the art, including, but not limited to, measuring angiogenic cytokine levels using PCR, as described in Example 3; using an enzyme-linked immunosorbent assay (ELISA), or radioimmunoassay (RIA), using antibody specific for individual angiogenic factors; and bioassays for specific individual angiogenic factors. See, e.g., Nicosia et al. (1994) *Am. J. Pathol.* 145:1023–1029; Morishita et al. (1999) *Hypertension* 33: 1379–1384; Koblizek et al. (1998) *Curr. Biol.* 8:529–532; Schraufnagel et al. (1992) *J. Thorac. Cardiovasc. Surg.* 104:1582–1588; and Yoshida et al. (1997) *Mol. Cell. Biol.* 17:4015–4023.

In some embodiments, the invention provides methods for increasing or stimulating the expression of angiogenic cytokine production. Administration of an effective amount of a pharmaceutically active relaxin to an individual in need thereof increases angiogenic cytokine production by at least about 10%, at least about 20%, at least about 30%, at least about 50%, at least about 75%, at least about 100% (or two-fold), at least about 2.5-fold, at least about 3-fold, at least about 5-fold, or at least about 10-fold or more, compared to a suitable control. Angiogenic factors include, but are not limited to, fibroblast growth factor (FGF), including acidic FGF, basic FGF; VEGF, including VEGF-A, VEGF-B, VEGF-C, and synthetic and recombinant forms which possess VEGF activity, specifically angiogenic activity; hepatocyte growth factor (HGF); platelet-derived growth factor (PDGF); placental growth factor; angiopoietin-1; proliferin; insulin-like growth factor-1; granulocyte colony stimulating factor (G-CSF); transforming growth factor-α; and interleukin-8. Whether angiogenic cytokine production is increased following relaxin administration can be assessed using any method known in the art, including, but not limited to, measuring angiogenic cytokine levels using polymerase chain reaction (PCR), as described in Example 3; using an enzyme-linked immunosorbent assay (ELISA), or radioimmunoassay (RIA), using antibody specific for individual angiogenic factors; and bioassays for specific individual angiogenic factors. See, e.g., Nicosia et al. (1994) *Am. J. Pathol.* 145:1023–1029; Morishita et al. (1999) *Hypertension* 33: 1379–1384; Koblizek et al. (1998) *Curr. Biol.* 8:529–532; Schraufnagel et al. (1992) *J. Thorac. Cardiovasc. Surg.* 104:1582–1588; and Yoshida et al. (1997) *Mol. Cell. Biol.* 17:4015–4023.

Thus, the invention provides methods of treating an ischemic condition. Administration of an effective amount of pharmaceutically active relaxin results in an increase in blood supply to an ischemic tissue. Following administration of relaxin, blood supply (blood flow) to the ischemic tissue is increased by at least about 10%, at least about 20%, at least about 30%, at least about 50%, at least about 75%, or at least about 100%, or more when compared to a suitable control. Whether the blood supply to an ischemic tissue is increased can be measured by any method known in the art, including, but not limited to, thermography; infrared recorder; transcutaneous $PO_2$, transcutaneous $PCO_2$, laser Doppler, Doppler waveform, ankle brachial index, pulse volume recording, toe pressure, duplex waveform, magnetic resonance imaging profile, isotope washout, and NAD/NADH fluorometry. Such methods are well known in the art and have been described in numerous publications, including, e.g., Lazarus et al. ((1994) *Arch. Dermatol.* 130:491) and references cited therein.

In some embodiments, methods are provided for promoting or enhancing wound healing. Administration of an effective amount of a pharmaceutically active relaxin to an individual in need thereof promotes wound healing by at least about 10%, at least about 20%, at least about 30%, at least about 50%, at least about 75%, or at least about 100%, or more when compared to a suitable control, e.g., the amount of necrotic tissue in the wound is decreased by at least about 10%, at least about 20%, at least about 30%, at least about 50%, at least about 75%, or at least about 100%, or more when compared to a suitable control. Whether administration of relaxin promotes wound healing can be determined using any method known in the art, including, but not limited to, the methods described in Example 4. For example, the amount of necrotic tissue can be measured; and/or histochemical evaluation of a tissue biopsy can be conducted to determine the presence of and/or to measure the amount of tissue necrosis.

In some embodiments, methods are provided for reducing angiotensin II (AngII)-mediated vasoconstriction. Administration of an effective amount of a pharmaceutically active relaxin to an individual in need thereof reduces AngII-mediated vasoconstriction by at least about 10%, at least about 20%, at least about 30%, at least about 50%, at least about 75%, or at least about 100%, or more when compared to a suitable control. Whether administration of relaxin reduces AngII-mediated vasoconstriction can be determined using any method known in the art for measuring vasodilation.

In some embodiments, methods are provided for reducing ET-1-mediated vasoconstriction. Administration of an effective amount of a pharmaceutically active relaxin to an individual in need thereof reduces ET-1-mediated vasoconstriction by at least about 10%, at least about 20%, at least about 30%, at least about 50%, at least about 75%, or at least about 100%, or more when compared to a suitable control. Whether administration of relaxin reduces ET-1-mediated vasoconstriction can be determined using any method known in the art for measuring vasodilation. In some embodiments, the methods comprise increasing endothelin type B receptor activation in a cell in a blood vessel by administering relaxin to the individual. Methods of determining whether endothelin type B receptor activation has been achieved are described in Example 2. Cells in a blood vessel that would be expected to be affected include, but are not limited to, endothelial cells, and smooth muscle cells.

Administration of relaxin in the hypoxic rat model of pulmonary hypertension described in Example 5 resulted in decreased extracellular matrix (ECM) synthesis in the vessel wall. Thus, in some embodiments, methods are provided for reducing ECM deposition in the vessel wall by at least about 2%, at least about 5%, at least about 10%, at least about 20%, at least about 30%, or at least about 50% or more when compared to a suitable control.

The methods of the present invention are suitable for treating an individual who has been diagnosed with a disease related to vasoconstriction, who is suspected of having a disease related to vasoconstriction, who is known to be susceptible and who is considered likely to develop a disease related to vasoconstriction, or who is considered likely to develop a recurrence of a previously treated disease relating to vasoconstriction.

Methods of treating diseases related to vasoconstriction can be enhanced by administering relaxin in combination with a known vasodilator and/or known angiogenic compounds. Methods of treating wounds can be enhanced by administering relaxin in combination with known vasodilator and/or angiogenic compounds.

RELAXIN FORMULATIONS

Relaxin formulations suitable for use in the methods of the invention are pharmaceutical formulations comprising a therapeutically effective amount of pharmaceutically active relaxin, and a pharmaceutically acceptable excipient. The formulation is preferably injectable and most preferably designed for intravenous injection.

Any known relaxin formulation can be used in the methods of the present invention, provided that the relaxin is pharmaceutically active. "Pharmaceutically active" relaxin is a form of relaxin which results in increased vasodilation and/or increased angiogenesis when administered to an individual.

Relaxin may be administered as a polypeptide, or as a polynucleotide comprising a sequence which encodes relaxin. Relaxin suitable for use in the methods of the present invention can be isolated from natural sources, may be chemically or enzymatically synthesized, or produced using standard recombinant techniques known in the art. Examples of methods of making recombinant relaxin are found in various publications, including, e.g., U.S. Pat. Nos. 4,835,251; 5,326,694; 5,320,953; 5,464,756; and 5,759,807.

Relaxin suitable for use includes, but is not limited to, human relaxin, recombinant human relaxin, relaxin derived from non-human mammals, such as porcine relaxin, and any of a variety of variants of relaxin known in the art. Relaxin, pharmaceutically active relaxin variants, and pharmaceutical formulations comprising relaxin are well known in the art. See, e.g., U.S. Pat. Nos. 5,451,572; 5,811,395; 5,945,402; 5,166,191; and 5,759,807, the contents of which are incorporated by reference in their entirety for their teachings relating to relaxin formulations, and for teachings relating to production of relaxin. In general, recombinant human relaxin (rhRLX) is identical in amino acid sequence to the naturally occurring product of the human H2 gene, consisting of an A chain of 24 amino acids and a B chain of 29 amino acids.

Relaxin can be administered to an individual in the form of a polynucleotide comprising a nucleotide sequence which encodes relaxin. Relaxin-encoding nucleotide sequences are known in the art, any of which can be used in the methods described herein. See, e.g. GenBank Accession Nos. AF135824; AF076971; NM_006911; and NM_005059. The relaxin polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly, Cancer Gene Therapy (1994) 1:51–64; Kimura (1994) *Human Gene Therapy* 5:845–852; Connelly (1995) *Human Gene Therapy* 1:185–193; and Kaplitt (1994) *Nature Genetics* 6:148–153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5,219,740; WO 93/11230; WO 93/10218; Vile and Hart (1993) *Cancer Res.* 53:3860–3864; Vile and Hart (1993) *Cancer Res.* 53:962–967; Ram et al. (1993) *Cancer Res.* 53:83–88; Takamiya et al. (1992) *J. Neurosci. Res.* 33:493–503; Baba et al. (1993) *J. Neurosurg.* 79:729–735; U.S. Pat. No. 4,777,127; and EP 345,242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

Gene delivery vehicles of the present invention can also employ parvovirus such as adeno-associated virus (AAV) vectors. Representative examples include the AAV vectors disclosed by Srivastava in WO 93/09239, Samulski et al. (1989) *J. Vir.* 63:3822–3828; Mendelson et al. (1988) *Virol.* 166:154–165; and Flotte et al. (1993) *Proc. Natl. Acad. Sci. USA* 90:10613–10617.

Also of interest are adenoviral vectors, e.g., those described by Berkner, Biotechniques (1988) 6:616–627; Rosenfeld et al.(1991) *Science* 252:431–434; WO 93/19191; Kolls et al. (1994) *Proc. Natl. Acad. Sci. USA* 91:215–219; Kass-Eisler et al. (1993) *Proc. Natl. Acad. Sci. USA* 90:11498–11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) *Hum. Gene Ther.* 3:147–154; ligand linked DNA, for example see Wu (1989) *J. Biol. Chem.* 264:16985–16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) *Mol. Cell Biol.* 14:2411–2418, and in Woffendin (1994) *Proc. Natl. Acad. Sci.* 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Further non-viral delivery suitable for use includes mechanical delivery systems such as the approach described in Woffendin et al. (1994) *Proc. Natl. Acad. Sci. USA* 91:11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

In general, a daily dose of relaxin may be from about 0.1 to 500 µg/kg of body weight per day, from about 6.0 to 200 µg/kg, or from about 12 to 100 µg/kg. In some embodiments, it is desirable to obtain a serum concentration of relaxin at or above about 1.0 ng/ml, from about 0.5 to about 50 ng/ml, from about 1 to about 20 ng/ml. For administration to a 70 kg person, a dosage may be in a range of from about 2 µg to about 2 mg per day, from about 10 µg to 500 µg per day, or from about 50 µg to about 100 µg per day. The amount of relaxin administered will, of course, be dependent on the subject and the severity of the affliction, the manner and schedule of administration and the judgment of the prescribing physician.

In employing relaxin for treatment of diseases relating to vasoconstriction, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and relaxin. In addition, these compositions may include other active agents (e.g., other angiogenic agents, other vasodilation-promoting agents), carriers, adjuvants, etc. Generally, depending on the intended mode of administration, the pharmaceutically acceptable composition will contain about 0.1% to 90%, about 0.5% to 50%, or about 1% to about 25%, by weight of relaxin, the remainder being suitable pharmaceutical excipients, carriers, etc. Actual methods of preparing such dosage forms are known, or will be apparent, to those skilled in this art; for example, see Remington's Pharmaceutical Sciences, Mack Publishing Company, Easton, Pa., 15th Edition, 1995. The formulations of human relaxin described in U.S. Pat. No. 5,451,572, are non-limiting examples of suitable formulations which can be used in the methods of the present invention.

Parenteral administration is generally characterized by injection, either subcutaneously, intradermally, intramuscularly or intravenously, or subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. In general, the composition will comprise 0.2–2% of the relaxin in solution.

Parenteral administration may employ the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Drug release devices suitable for use in administering relaxin according to the methods of the invention may be based on any of a variety of modes of operation. For example, the drug release device can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump, are also suitable for use with the present invention. Examples of such devices include those described in, for example, U.S. Pat. Nos. 4,692,147; 4,360,019; 4,487,603; 4,360,019; 4,725,852, and the like. In general, the present treatment methods can be accomplished using any of a variety of refillable, non-exchangeable pump systems. Osmotic pumps have been amply described in the literature. See, e.g., WO 97/27840; and U.S. Pat. Nos. 5,985,305 and 5,728,396.

Relaxin may be administered over a period of hours, days, weeks, or months, depending on several factors, including the severity of the disease being treated, whether a recurrence of the disease is considered likely, etc. The administration may be constant, e.g., constant infusion over a period of hours, days, weeks, months, etc. Alternatively, the administration may be intermittent, e.g., relaxin may be administered once a day over a period of days, once an hour over a period of hours, or any other such schedule as deemed suitable.

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 micrometers, preferably less than 10 micrometers.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Relaxin is a Potent Renal Vasodilator in Conscious Rats

Materials and Methods

Animal Preparation

Long-Evans female rats aged 10–14 weeks were purchased from Harlan Sprague-Dawley (Frederick, Md.). They were fed PROLAB RMH 2000 diet containing 0.48% sodium (PME Feeds Inc., St. Louis, Mo.) and provided water ad libitum. To prepare the rats for experimental procedures, they were trained for several hours in a Plexiglas restraining cage (Braintree Scientific Co., Braintree, Mass.) on at least five different occasions before surgical intervention. These cages afforded sufficient space for grooming of the face and front paws while preventing the rat from turning around. Thus, accurate timed-urine collections and blood samplings were made possible from the chronically implanted bladder and vascular catheters, respectively. Rats failing to habituate to the cage were eliminated from the study (<1%). All animal procedures were approved by the Institutional Animal Care and Use Committee of the Magee-Womens Research Institute.

The details of the surgical procedures have been previously described. See, e.g., Conrad (1984) *Kidney Int.* 26:24–29; and Danielson and Conrad (1995) *J. Clin. Invest.* 96:482–490. Briefly, using ketamine (6.0 mg/100 g body weight) and pentobarbital sodium (2.1 mg/100 g body weight) anesthesia, Tygon catheters were implanted in the abdominal aorta and inferior vena cava via the femoral artery and vein, respectively. The bladder catheter, a silastic-covered stainless steel cannula, was sewn into the urinary bladder with a purse-string suture and exteriorized through the ventral abdominal wall. This catheter was then plugged allowing the animal to urinate through the urethra while in her home cage. In the ovariectomized and sham ovariectomized animals, the ovaries were first ligated and then excised, or briefly manipulated, respectively, via a small incision made in the lateral abdominal wall immediately after the insertion of vascular and bladder catheters. All surgeries were conducted using aseptic technique. At least a 7-day recovery period was allowed before experimentation.

For chronic infusion of relaxin, an osmotic minipump was inserted subcutaneously (s.c.) in the back of the animal under ether anesthesia. After shaving and cleaning the skin with alcohol and betadine, a small incision was made and the minipump containing either recombinant human relaxin (rhRLX), purified porcine relaxin (RLX), or vehicle was inserted. Then the incision was closed with surgical staples. The model 2001 and 2ML1 osmotic minipumps (Alza Co., Palo Alto, Calif.) were used for the purified porcine RLX and rhRLX, respectively.

Influence of chronic infusion of purified porcine RLX, rhRLX, or vehicle on renal function in intact, female rats.

At the beginning of each experiment, immediately after opening the arterial catheter and before infusion of fluids, 100 µl of blood was collected into a heparinized tube. After centrifugation to separate blood cells from plasma, the latter was frozen at −20° C. until assay for osmolality. Then, three 30-minute baseline urine collections with midpoint blood samples and continuous recording of MAP were made on one or two occasions separated by at least 48 hours, in order to accurately measure control MAP, GFR, ERPF, and ERVR (MAP/ERPF). The hematocrit was also routinely determined on these midpoint blood samples. The renal clearances of IN and PAH were used to assess GFR and ERPF, respectively. The femoral arterial catheter was connected to a Statham pressure transducer (Gould P23 ID, Statham Instruments, Hato Rey, PR) and a Gould Universal amplifier for measurement of MAP, which was displayed on a Gould 5900 Series Signal Conditioner Cage and TA11 chart recorder. Next, an osmotic minipump containing purified porcine RLX (4 µg/hour; n=7 rats), rhRLX (4 µg/hour; n=5) or vehicle (n=4) was implanted. MAP, GFR, ERPF, and ERVR were assessed on days 2 and 5 of the infusion, and 5–12 days after depletion of the 7-day minipump. Details of our methodologies for the assessment of GFR and ERPF in chronically instrumented, conscious rats including the measurement of IN and PAH in both plasma and urine have been previously published. Conrad (1984) *Kidney Int.* 26:24–29; and Danielson and Conrad (1995) *J. Clin. Invest.* 96:482–490. Circulating relaxin concentrations of 20–40 ng/mL have been measured in rats of 12–14 gestational days. Sherwood et al. (1980) *Endocrinol.* 107:691–698. An infusion rate of 4 µg/hour for purified porcine RLX or rhRLX would be expected to produce plasma levels of 20–40 ng/mL.

Influence of chronic infusion of rhRLX on renal function in ovariectomized or sham ovariectomized rats.

Six female rats each were subjected either to ovariectomy or sham ovariectomy immediately after the implantation of vascular and bladder catheters. Seven days later, renal function and MAP were assessed before the insertion of osmotic minipumps containing rhRLX. On day 5 of the relaxin infusion (4 µg/hour), renal function and MAP were again determined.

Acute infusion of L-NAME or Angiotensin II during chronic infusion of purified porcine RLX.

At least 7 days after the implantation of vascular and bladder catheters, osmotic minipumps containing either porcine RLX (4 µg/hour) or vehicle (Ringer's solution) were implanted in intact, female rats (n=7 and 6 rats, respectively). Renal function and MAP were measured on day 5 of relaxin infusion (three 30-minute urine and midpoint blood collections). Next, an infusion of L-NAME (2 µg/minute, a substrate competitive inhibitor of NO synthase) was administered intravenously (i.v.) by infusion pump (Model 200, KD Scientific, Boston, Mass.). Four 1-hour urine collections with midpoint blood samples were collected for the assessment of GFR, ERPF, and ERVR during the L-NAME administration. Identical procedures were performed on additional animals chronically administered porcine RLX (n=5) or vehicle (n=5), except that ANG II (3 ng/minute) was infused rather than L-NAME. Finally, another four, age-matched control rats were administered Ringer's solution instead of either L-NAME or ANG II on day 5 of porcine RLX infusion.

Metabolic cage studies.

Six rats were individually housed in Nalgene metabolism cages (Rodent Metabolism Cages for 150–300 g rats, VWR Scientific). Water and food were provided ad libidum. After 5–7 days of habituation, two baseline 24-hour urine collections were obtained. Then, an osmotic minipump containing purified porcine RLX was implanted (4 µg/hour). Additional 24-hour urine collections were made on days 2 and 5 of relaxin infusion and on days 4, 12, and 25 after exhaustion of the 7-day minipump. Food and water intake, as well as urinary flow rate were measured by gravimetric technique. The urinary excretion of sodium, cyclic guanosine monophosphate, and NOx were also determined. The measurements made during the two baseline collections were averaged, as were the measurements made during the three post-relaxin collections.

Analytic techniques.

Plasma osmolality was measured using a freezing-point depression instrumentation osmometer (Model 3MO, Advanced Instruments, Needham Heights, Mass.). Plasma and urine IN and PAH were assayed by standard techniques. Urinary sodium concentration was measured by ion selective electrode (Sodium-Potassium Chemistry Module, Beckman Instruments, Inc., Brea, Calif.). Urinary cGMP was determined by specific radioimmunoassay as previously described. Conrad and Vernier (1989) *Am. J. Physiol.* 257:R847–R853. Urinary $NO_x$ was measured by reduction of nitrate to nitrite, the latter determined by the Griess reaction which produces a calorimetric product measured at 540 nm (Nitrate/Nitrite Colorimetric Assay Kit, Cayman Chemical, Ann Arbor, Mich.).

One milliliter of blood was obtained from the rats administered rhRLX for 5 days at the end of the renal function measurements. The levels of rhRLX in serum were then measured in a quantitative sandwich immunoassay. Unemori et al. (1996) *J. Clin. Invest.* 98:2739–2745. Briefly, wells of a 96-well microtiter plate (Maxisorp Immunomodules, Nunc, Inc., Naperville, Ill.) were coated overnight with affinity purified anti-rhRLX rabbit polyclonal antibody. Sera were diluted in phosphate buffered saline containing Tween 20, Thimerosal, bovine serum albumin (Sigma Chemical Co., St. Louis, Mo.) and normal goat IgG (Organon Teknika-Cappel, Durham, N.C.), and 100 µl were added to wells in duplicate. After an overnight incubation at 4° C., the wells were washed and 100 µl of affinity-purified, peroxidase-conjugated, anti-rhRLX rabbit polyclonal antibody was added to each well. After an appropriate incubation period at room temperature, the wells were washed again, and 100 µl of a tetramethylbenzidine solution was added to each well. After color development, the reaction was stopped, absorbances at 450/630 nm were measured, and relaxin concentrations in the sera were determined by entering data into a four-parameter logistic curve-fitting program. The assay has been validated for use with murine serum, shows no detectable cross-reactivity with natural murine relaxin, and has a lower detection limit of 20 pg/ml.

Preparation of drugs.

PAH and IN were freshly prepared on the morning of the experiment using Ringer's solution as diluent. Inulin, characteristically insoluble at ambient temperature, was prepared for infusion by heating a 15 ml aliquot in a boiling water bath for 10 minutes. When diluted in Ringer's solution and mixed with PAH, it remained in solution throughout the experiment. L-NAME (Sigma Chemical, St. Louis, Mo.) was also prepared in Ringer's solution within an hour of use. ANG II (5-ILE AII or Hypertensin II; Sigma Chemical, St. Louis, Mo.) was prepared from a stock solution in 5% dextrose (100 µg/ml) which was frozen in aliquots at −20° C. Final dilutions were made in Ringer's solution immediately before infusion. For chronic infusion by osmotic minipump, rhRLX (Connetics, Palo Alto, Calif.) was prepared from a stock 1.5 mg/mL solution in 20 mM sodium acetate, pH 5.0, and diluted accordingly in the same buffer, and the lyophilized, purified porcine RLX (Sherwood and O'Byrne (1974) *Arch. Biochem. Biophys* 160:185–196) was dissolved in Ringer's solution. For acute infusion, the lyophilized purified porcine RLX was prepared daily immediately prior to use in Ringer's solution containing 0.01% rat albumin (Cappel Research Products, Durham, N.C.).

Statistical analysis.

Statistical analyses were carried out essentially as described. Zar (1984) *Biostatistical Analysis* Prentice Hall, N.J. Data are presented as mean±SEM. Most data were analyzed using repeated measures mixed models with treatment group and time as fixed effects. If significant main effects or interactions were observed, then Dunnett's test was used to compare least-squares means for baseline values with all subsequent time periods. Least-squares means for rats administered vehicle, recombinant human and purified porcine RLX were compared using Scheffe's procedure for multiple comparisons. For Table 5 (see below), one factor repeated measures ANOVA was used, and group means were compared by Orthogonal Contrasts. A p-value of <0.05 was considered to be significant.

Results

Chronic infusion of rhRLX, purified porcine RLX, or vehicle (FIGS. 1A–D)

The time control experiments using either the vehicle for rhRLX (20 mM sodium acetate, pH 5.0, n=2 rats) or the vehicle for porcine RLX (Ringer's solution, n=2 rats) showed relative stability of MAP, GFR, ERPF and ERVR over the two week or so study period (p=NS by ANOVA). Because the results obtained with the two different vehicle preparations were comparable, they were combined. While chronic infusion of purified porcine RLX at 4 µg/hour did not significantly change MAP, there was a marked increase in GFR and ERPF, as well as a reciprocal reduction in ERVR on both days 2 and 5 of administration (p<0.05 vs baseline and vehicle). Similar results were obtained for rhRLX, except that significance was not reached until day 5 of infusion.

Chronic infusion of rhRLX in ovariectomized or sham ovariectomized rats (FIGS. 2 A–D).

The profound rise in GFR and ERPF, as well as fall in ERVR observed on day 5 of relaxin infusion were comparable in ovariectomized and sham ovariectomized rats (p=NS).

Acute infusion of L-NAME or ANG II during chronic infusion of purified porcine RLX.

The renal vasodilation and hyperfiltration in the relaxin-treated rats observed on day 5 of infusion was completely abrogated by NO synthase inhibition, as shown in Table 1. Table 1 shows the effect of L-NAME on Mean Arterial Pressure (MAP) and function in conscious rats administered porcine RLX or Ringer' Solution (vehicle) for 5 days. MAP, GFR, ERPF, and ERVR were measured at time zero (baseline), and at 60, 120, 180, and 240 minutes after administering L-NAME and either RLX or vehicle alone. Values represent the mean±SEM. L-NAME (Nω-nitro-L-arginine methyl ester) was infused at 2 µg/minute intravenously, and relaxin was administered at 4 µg/hour by osmotic minipump subcutaneously. There were 7 and 6 rats, respectively, in the RLX and vehicle groups. An asterisk denotes p<0.05; the symbol H denotes p<0.05 for RLX vs. vehicle.

TABLE 1

|  | Baseline | 60 min | 120 min | 180 min | 240 min |
|---|---|---|---|---|---|
| MAP |  |  |  |  |  |
| RLX | 120 ± 2 | 135 ± 5*† | 136 ± 4*† | 136 ± 4*† | 139 ± 4*† |
| Vehicle | 117 ± 4 | 122 ± 4 | 126 ± 4 | 129 ± 4* | 129 ± 3* |
| GFR |  |  |  |  |  |
| RLX | 3050 ± 95† | 2776 ± 142 | 2653 ± 207 | 2498 ± 113* | 2392 ± 50* |
| Vehicle | 2383 ± 72 | 2419 ± 170 | 2153 ± 122 | 2350 ± 63 | 2250 ± 88 |
| ERPF |  |  |  |  |  |
| RLX | 10245 ± 260† | 7520 ± 481* | 7030 ± 419* | 6530 ± 270* | 5973 ± 195* |
| Vehicle | 7241 ± 350 | 7301 ± 385 | 6452 ± 216* | 6595 ± 507* | 6187 ± 317* |
| ERVR |  |  |  |  |  |
| RLX | 6.96 ± 0.23† | 11.00 ± 0.57* | 11.87 ± 0.76* | 12.92 ± 0.66* | 14.13 ± 0.47* |
| Vehicle | 10.48 ± 0.29 | 10.53 ± 0.58 | 12.28 ± 0.58 | 12.46 ± 0.92 | 12.64 ± 0.73 |

To minimize the possibility that the convergence of renal function in the relaxin and vehicle infused rats elicited by L-NAME was merely a consequence of nonspecific renal vasoconstriction, the experimental paradigm was repeated using another vasoconstrictor, ANG II. Rather than converging, ERPF and ERVR diverged even further during the acute infusion of angiotensin II, as shown in Table 2. Values are provided as mean±SEM. Relaxin, RLX; Angiotensin II, ANG II. ANG II was infused at 3 ng/min i.v., and RLX at 4 µg/h by osmotic minipump s.c. There were five rats each in the RLX and vehicle groups. *p<0.05 vs baseline, Hp<0.05 RLX vs vehicle.

TABLE 2

|  | Baseline | 60 min | 120 min | 180 min | 240 min |
|---|---|---|---|---|---|
| MAP |  |  |  |  |  |
| RLX | 111 ± 3 | 130 ± 5* | 142 ± 4* | 143 ± 5* | 146 ± 6* |
| Vehicle | 112 ± 5 | 131 ± 8 | 140 ± 9 | 144 ± 9* | 145 ± 9* |
| GFR |  |  |  |  |  |
| RLX | 2929 ± 120† | 2980 ± 219† | 2653 ± 169† | 2578 ± 169 | 2763 ± 155† |
| Vehicle | 2252 ± 63 | 2339 ± 123 | 2091 ± 127 | 2297 ± 59 | 1934 ± 67 |
| ERPF |  |  |  |  |  |
| RLX | 10364 ± 411† | 8926 ± 478† | 9646 ± 772† | 7738 ± 386*† | 7698 ± 592*† |
| Vehicle | 7213 ± 487 | 5689 ± 453* | 5127 ± 369* | 4493 ± 468* | 4053 ± 118* |

TABLE 2-continued

|  | Baseline | 60 min | 120 min | 180 min | 240 min |
|---|---|---|---|---|---|
| ERVR |  |  |  |  |  |
| RLX | 6.23 ± 0.41† | 8.88 ± 0.66*† | 9.24 ± 1.03*† | 11.52 ± 0.84*† | 11.84 ± 1.08*† |
| Vehicle | 9.03 ± 0.54 | 14.07 ± 1.69 | 16.59 ± 1.76* | 20.53 ± 2.31* | 21.81 ± 1.56* |

Thus, these results were diametrically opposed to those obtained using the L-NAME. L-NAME produces a significantly greater rise in MAP and ERVR, and reduction in GFR and ERPF in the relaxin-treated compared to vehicle infused rats (p<0.05 by ANOVA). In contrast, the percent increase in MAP and reduction in GFR elicited by ANG II was comparable in the RLX treated and vehicle infused rats, whereas the percent increase in ERVR and reduction in ERPF was markedly attenuated in the rats administered chronic relaxin (p<0.001 vs. vehicle by ANOVA). Another group of rats chronically treated with porcine RLX was administered Ringer's solution instead of L-NAME or ANG II, and thus served as time controls. Neither MAP nor any of the renal parameters were consistently altered over the 6 hours or so of vehicle infusion, as shown in Table 3. Values are provided as mean±SEM. Relaxin, RLX. n=4 rats. Ringer's solution was infused at the same flow rate as L-NAME (Table 1) or ANG II (Table 2), 12.5 μl/min. RLX was infused at 4 μg/hour by osmotic minipump s.c.

TABLE 3

|  | Baseline | 60 min | 120 min | 180 min | 240 min |
|---|---|---|---|---|---|
| MAP |  |  |  |  |  |
| RLX | 119 ± 2 | 123 ± 3 | 121 ± 4 | 122 ± 4 | 121 ± 4 |
| GFR |  |  |  |  |  |
| RLX | 2997 ± 98 | 3008 ± 243 | 3086 ± 143 | 3077 ± 127 | 3223 ± 121 |
| ERPF |  |  |  |  |  |
| RLX | 12,927 ± 804 | 12,630 ± 1140 | 12,347 ± 1303 | 12,353 ± 1266 | 12,090 ± 439 |
| ERVR |  |  |  |  |  |
| RLX | 5.93 ± 0.35 | 6.19 ± 0.48 | 6.40 ± 0.64 | 6.52 ± 0.68 | 6.53 ± 0.24 |

Hematocrit and plasma osmolality

In the intact, female rats chronically administered either purified porcine or rhRLX for the study of renal function, both the hematocrit and plasma osmolality showed significant decrements by day 2 (p<0.05). The results are shown in Table 4. Data are presented as mean±SEM. rhRLX, recombinant human relaxin. RLX was infused at 4 μg/h by osmotic minipump s.c. There were 7, 4, and 5 rats, respectively, in the porcine RLX, vehicle, and rhRLX groups at baseline, and days 2 and 5 of treatment. During the post RLX period, 6, 2, and 2 rats were studied in the porcine RLX, vehicle and rhRLX groups. Two of the rats in the vehicle group received Ringer's solution (vehicle for porcine RLX), and two received 20 mM sodium acetate, pH 5.0 (vehicle for rhRLX). The results were not different, and therefore, the data were combined. *p<0.05 vs baseline, Hp<0.05 RLX vs vehicle.

TABLE 4

|  | Baseline | Day 2 | Day 5 | Post RLX Day 5–12 | Difference between baseline and Day 5 |
|---|---|---|---|---|---|
| Hematocrit (%) | | | | | |
| Porcine RLX | 42 ± 1 | 39 ± 1* | 37 ± 1*† | 40 ± 1 | −4 ± 1† |
| Vehicle | 40 ± 3 | 39 ± 1 | 40 ± 1 | 41 | +2 ± 3 |
| rhRLX | 39 ± 0 | 37 ± 1* | 37 ± 1*† | 40 | −2 ± 1† |
| Plasma osmolality (mOsm/kg $H_2O$) | | | | | |
| Porcine RLX | 301 ± 2 | 289 ± 2*† | 287 ± 2*† | 299 ± 2 | −14 ± 3† |
| Vehicle | 298 ± 3 | 297 ± 2 | 299 ± 3 | 299 | 0 ± 2 |
| rhRLX | 299 ± 2 | 291 ± 3*† | 286 ± 2*† | 302 | −12 ± 2† |

Urinary excretion of cGMP and $NO_X$.

The 24-hour urinary excretion of cGMP and $NO_X$ were not significantly affected by the chronic infusion of porcine RLX at 4 μg/hour (p=NS by ANOVA). In the same animals, urinary sodium excretion and water intake were significantly increased on days 2 and 5, respectively, of relaxin infusion (p<0.05 vs baseline and post RLX). The results are shown in Table 5. Values represent mean±SEM. Relaxin, RLX; $NO_X$, nitrate+nitrite; cyclic guanosine-3',5'-monophosphate, cGMP. n=6 rats. RLX was infised at 4 μg/hour by osmotic minipump s.c. *p<0.05 vs baseline and post RLX.

TABLE 5

|  | Baseline | Day 2 | Day 5 | Post-relaxin day 4–18 |
|---|---|---|---|---|
| Food intake (g) | 13.2 ± 1.0 | 15.5 ± 1.5 | 16.7 ± 1.0 | 15.3 ± 0.5 |
| Water intake (mL) | 19.1 ± 2.7 | 20.1 ± 3.4 | 23.6 ± 3.3* | 19.1 ± 2.6 |
| Urine output (ml/24 hours) | 9.1 ± 1.7 | 11.4 ± 2.2 | 8.8 ± 0.9 | 9.1 ± 1.1 |
| Urinay sodium excretion (μEq/24hours) | 438.8 ± 34.4 | 800.2 ± 77.2* | 477.8 ± 57.9 | 480.69 ± 54.4 |
| Urinary cGMP excretion (nmole/24 hours) | 32.2 ± 1.9 | 26.5 ± 2.5 | 28.6 ± 3.8 | 32.7 ± 3.8 |
| Urinary NOx excretion (μmole/24hours) | 4.8 ± 0.5 | 6.0 ± 1.0 | 5.9 ± 0.7 | 6.1 ± 0.9 |

Serum relaxin.

In 17 of the rats, we measured the serum concentration of the rhRLX that was infused by osmotic minipump at 4 μg/hour for 5 days. The mean±SEM was 28.1±4.8 ng/mL.

Example 2

Impact of Gender and Endothelin on Renal Vasodilation and Hyperfiltration Induced by Relaxin in Conscious Rats

Methods

Animal preparation.

Long Evans female and male rats of 10–14 weeks of age were used. Those animals studied at the University of New Mexico were purchased from Harlan Sprague-Dawley (Indianapolis, Ind.) and were fed PROLAB RMH 2500 diet containing 0.40% sodium (PME Feeds Inc., St. Louis, Mo.). The rats investigated at the Magee-Womens Research Institute were purchased from Harlan Sprague-Dawley (Frederick, Md.) and they were fed PROLAB RMH 2000 diet containing 0.48% sodium (PME Feeds Inc., St. Louis Mo.). The rats were maintained on a 12 hour light/dark cycle in fully accredited Animal Resource Facilities approved by the Association for Assessment and Accreditation of Laboratory Animal Care. All experiments were approved by the Institutional Animal Care and Use Committee of the University of New Mexico School of Medicine or the Magee-Womens Research Institute.

Prior to surgical preparation, the rats were habituated to Plexiglass experimental cages (Braintree Scientific Co., Braintree Mass.) over 5 days. The first two training periods were short—approximately 1–2 hours each. For the last three sessions, the time was lengthened to match the duration of the experimental protocol. The cages permitted the rats to groom their face and paws, but prevented them from turning around, thus allowing for accurate, timed urine collections to be made (see below). Any rats failing to adapt to the experimental cage were eliminated from the study (<5%).

The surgical procedures have been previously described in detail. Conrad (1984) *Kidney Int.* 26:24–29; Conrad and Colpoys (1986) *J. Clin. Invest.* 77:236–245; Danielson and Conrad (1995) *J. Clin. Invest.* 96:482–490; and Danielson and Conrad (1996) *Circ. Res.* 79:1161–1166. Briefly, while under general anesthesia using ketamine (6.0 mg/100 g BW intramuscularly (i.m.)) and sodium pentobarbital (2.1 mg/100 g BW intraperitoneally (i.p.)) and aseptic technique, the rats were prepared with Tygon catheters (0.015 inch ID and 0.030 inch OD, Norton Performance Plastics, Akron Ohio) implanted in the abdominal aorta and inferior vena cava via the femoral artery and vein, respectively. The catheters were tunneled subcutaneously and exteriorized between the scapulae. After filling them with a 1:1 mixture of sodium heparin (1000 U/ml) and 50% dextrose, the catheters were plugged with stainless steel pins. The urinary bladder was then exposed through an abdominal incision and a stainless steel catheter covered by a silastic sheathing with flanges was inserted into the bladder through a small incision at the base and secured with a purse-string suture. The bladder catheter was exteriorized through the muscle layers and skin of the ventral abdominal wall, and stoppered with a removable silastic coated obturator that allowed the rat to urinate normally through the urethra while in the home cage. After surgery, the rats were returned to their home cages and provided 5% dextrose in water during the first 2 days of surgical recovery for additional hydration and nourishment. Seven-10 days of recovery were permitted during which time the rats were trained once more to the experimental cage.

Experimental protocol—male rats.

After being placed in the experimental cage, a 100 $\mu$l blood sample was drawn from the arterial catheter into a heparinized tube for measurement of baseline plasma osmolality, sodium concentration and hematocrit prior to the administration of any fluids. This catheter was subsequently connected to a Statham pressure transducer (Gould P23 ID) and a Gould Universal amplifier to measure mean arterial pressure (MAP) which was displayed on a Gould 5900 Series Signal Conditioner Cage and TA11 chart recorder. Next, a bolus of inulin (IN, 0.2 ml of a 20% stock solution/100 g BW) and para-aminohippurate (PAH, 0.1 ml of a 2% working solution/100 g BW) was given over 1 minute into the venous catheter followed by a constant infusion of the two reagents at a rate of 0.5 mg/minute per 100 g BW and 0.1 mg/minute per 100 g BW, respectively. The flow rate was 19 $\mu$l/minute delivered by a Model 200 Syringe Pump (kd Scientific, Boston Mass.). Finally, the obturator in the bladder catheter was removed, and the latter was extended with a short piece of polyethylene tubing to facilitate the collection of urine.

After an equilibration period of 60 minutes, three 30 minute urine collections with midpoint blood samples were obtained, in order to determine the renal clearances of IN and PAH which provide measures of glomerular filtration rate (GFR) and effective renal blood flow (ERPF), respectively. The technique of urine collection has proven to be reliable. Conrad and Colpoys (1986) *J. Clin. Invest.* 77:236–245; Danielson and Conrad (1995) *J. Clin. Invest.* 96:482–490; and Danielson and Conrad (1996) *Circ. Res.* 79:1161–1166. Indeed, after reaching steady-state in this study, the excretion rates of IN and PAH were 91±3 and 100±4% of their respective infusions. After measuring baseline mean arterial pressure and renal function, an osmotic minipump (model 2ML1, Alza Co., Palo Alto Calif.) containing either recombinant human relaxin (rhRLX; n=12 rats) or vehicle (n=7) was implanted subcutaneously on the back using light ether anesthesia. The infusion rate of rhRLX was 4 $\mu$g/hour, a rate which produces serum levels comparable to midgestation in the female rat when effective renal plasma flow and glomerular filtration rate are maximal during pregnancy in this species (see Results, below). Five days later, mean arterial pressure (MAP), glomerular filtration rate (GFR), effective renal plasma flow (ERPF), and other parameters were again assessed as describe above. At this time, the excretion rates of IN and PAH were 91±3 and 98±2% of their respective infusion rates. At the end of the experiment, 1.0 ml of blood was collected for determination of serum rhRLX.

Experimental protocol—female rats.

After surgical recovery, an osmotic minipump (model 2ML1, Alza Co., Palo Alto Calif.) containing either recombinant human relaxin (rhRLX; n=9 rats) or vehicle (n=8) was implanted subcutaneously on the back using light ether anesthesia. The infusion rate of rhRLX was 4 $\mu$g/hour. Experiments were conducted on day 5 of rhRLX or vehicle administration. MAP and renal function were measured as described above.

After an equilibration period of 60 minutes, three 30 minute urine collections with midpoint blood samples were obtained, in order to determine baseline renal clearances of IN and PAH. The technique of urine collection was again reliable. After reaching steady-state, the excretion rates of IN and PAH at baseline were 99±3 and 100±2% of their respective infusions for the rats administered rhRLX, and 100±2 and 99±2% for those given vehicle. Following the determination of baseline MAP and renal function, an infusion of RES-701-1, a selective endothelin type B ($ET_B$) receptor antagonist (Conrad et al. (1999) *Am. J. Physiol.* 272:F767–F776; and Tanaka et al. (1994) *Mol. Pharmacol.* 45:724–730), was started at a rate of 10 μg/minute (flow rate 12 μl/minute) through the venous catheter. Next, six 40-minute renal clearances were obtained during the infusion of the RES-701-1. The average recovery rates for both IN and PAH in the urine were comparable to those described above, i.e., >95% of the infusion rates. At the end of the experiment, 1.0 ml of blood was collected for determination of serum rhRLX.

In an additional three rats each administered rhRLX or vehicle, identical experimental procedures as described above were applied, except that the vehicle for RES-701-1 was infused instead of RES-701-1.

Analytical techniques.

Inulin concentration in plasma and urine was measured by the anthrone method, and PAH was determined by the method of Bratton and Marshall as modified by Smith. This method is described in Conrad (1984) *Kidney Int.* 26:24–29, and references cited therein. Plasma sodium was measured by a Kodak Ektachem Instrument (Rochester, N.Y.). Plasma osmolality was determined by freezing point depression (Advanced Osmometer, Model 3MO, Advanced Instruments, Needham Heights Mass.). All urine and plasma samples from MWRI were coded and sent to UNM for analysis of IN, PAH, sodium and osmolality (by L.A.D.). The rhRLX in serum was measured using a quantitative sandwich immunoassay, again in a blinded fashion. Danielson et al. (1999) *J. Clin. Invest.* 103:525–533.

Preparation of drugs.

PAH (para-aminohippurate) (Merck and Co., Inc., West Point Pa.) and IN (inulin) (Cypros Pharmaceutical Corp., Carlsbad Calif.) were prepared on the morning of the experiment using Ringers solution as a diluent. IN, characteristically insoluble at room temperature, was prepared for infusion by heating the stock aliquots in a boiling water bath for 5–10 minutes until dissolved. When diluted and mixed with PAH and Ringers solution, IN remained in solution throughout the experiment. The rhRLX was at a concentration of 1.5 mg/ml in 20 mM sodium acetate (pH 5.0). The rhRLX was diluted with additional 20 mM sodium acetate for instillation in the osmotic minipumps, or the 20 mM sodium acetate buffer was administered alone as vehicle. The flow rate of the osmotic minipumps was approximately 10 μl/hour. The ET receptor antagonist RES-701-1—a selective $ET_B$ receptor subtype antagonist purified from the broth of Streptomyces sp., was prepared at 37° C. in a dilute 0.02% sodium carbonate solution containing 5% dextrose. Conrad et al. (1999) *Am. J. Physiol.* 272:F767–F776; and Tanaka et al. (1994) *Mol. Pharmacol.* 45:724–730.

Statistical analysis.

There were a total of 12 male rats administered rhRLX and 7 administered vehicle. Five of the rats receiving rhRLX and 3 given vehicle were studied at a laboratory independently from the remaining rats in the two groups, which were investigated by a second laboratory group. The data obtained from the two laboratories were comparable, and therefore, combined. Data are expressed as mean±SEM. MAP and renal function measured during the three renal clearance periods were averaged for each experiment. The results obtained at baseline and after 5 days of rhRLX or vehicle infusion were compared by paired t-tests (FIGS. 3 A–D). In Table 6, we applied unpaired t-tests. A p value of <0.05 was taken to be significant.

There were a total of 11 female rats administered rhRLX and 10 administered vehicle. Five in each group were studied at one laboratory; the remaining rats in the two groups were investigated at a second laboratory. The data obtained by the two laboratories were comparable, and therefore, combined. Data are expressed as mean±SEM. MAP and renal function measured during the three baseline renal clearance periods were averaged. The data obtained from the 6 renal clearance periods during the infusion of RES-701-1 or its vehicle were also averaged. Two factor repeated measures analysis of variance was employed to analyze the data presented in FIGS. 4A–D. If significant main effects or interactions were observed, then group means were compared by the method of Contrasts (SuperANOVA, Abacus Concepts, Inc., Berkeley Calif.). In Table 7, we used unpaired t-tests. A p value of <0.05 was again taken to be significant.

Results

Male rats.

The results for MAP and renal function are portrayed in FIGS. 3A–D. The chronic administration of rhRLX did not significantly affect MAP. In contrast, the hormone significantly increased both GFR and ERPF, while reducing effective renal vascular resistance (ERVR). The vehicle time-control studies showed stability of both MAP and renal function.

TABLE 6

| Rat group | HCT (%) | Posm (mOsm/kg $H_2O$) | $PNa^+$ (mEq/L) |
|---|---|---|---|
| Vehicle (n = 7 rats) | −1.8 ± 1.3 | 0.9 ± 1.4 | 0.6 ± 0.7 |
| rhRLX (n = 11 rats) | −5.0 ± 0.6* | −10.9 ± 1.4* | −5.3 ± 0.4* |

Table 6 depicts the data for hematocrit, plasma osmolality, and sodium concentration. Values presented are: HCT, hematocrit; Posm, plasma osmolality; $PNa^+$, plasma sodium concentration. Data represent change from the baseline and are given as the mean±SEM. Values marked with an asterisk indicate p<0.05. These variables were relatively constant in the vehicle time-control experiments. However, in those rats receiving rhRLX for 5 days, there was a significant decline in all three parameters.

Relaxin was not detectable in any of the rats that were administered vehicle (n=7). In those that were administered rhRLX, the mean concentration was 12.3±0.7 ng/ml (n=12).

Female rats.

FIGS. 4A–D portray the results using the specific $ET_B$ receptor antagonist, RES-701-1. At baseline, both GFR and ERPF were significantly increased, and ERVR reciprocally reduced by 20–30% in the rats administered rhRLX for 5 days compared to vehicle infusion. MAP was not significantly affected.

Administration of RES-701-1 had no significant effect on MAP and renal function in the vehicle treated rats, although ERVR tended to be increased. In contrast, RES-701-1 reduced both GFR and ERPF, and increased MAP and ERVR in the rats treated with rhRLX (all p<0.05 vs baseline). During the infusion of the $ET_B$ receptor antagonist, GFR, ERPF and ERVR converged in the two groups of rats by the end of the second renal clearance period.

TABLE 7

|  | MAP B | MAP V | GFR B | GFR V | ERPF B | ERPF V | ERVR B | ERVR V |
|---|---|---|---|---|---|---|---|---|
| Vehicle n = 3 rats | 113 ± 4 | 113 ± 6 | 2189 ± 108 | 2308 ± 26 | 6550 ± 206 | 7885 ± 668 | 10.36 ± 0.54 | 9,47 ± 0.70 |
| rhRLX n = 3 rats | 112 ± 7 | 115 ± 8 | 3082 ± 31* | 3112 ± 138* | 11220 ± 138* | 10464 ± 382* | 6.67 ± 0.56* | 6.97 ± 0.62* |

Table 7 depicts the data from the rhRLX or vehicle treated rats administered the vehicle for RES-701-1 instead of the antagonist (time-control). Values are given as mean±SEM. B, baseline; V, vehicle for RES-701-1. *$p<0.05$ rhRLX vs vehicle (for rhRLX). At baseline, GFR and ERPF were increased, and ERVR reduced in the rats administered rhRLX for 5 days compared to baseline values observed in the rats receiving vehicle instead of rhRLX (all $p<0.05$). These differences were maintained during the administration of the vehicle for RES-701-1 showing stability of renal function over the 240 min infusion period.

On day 5 of rhRLX administration, the mean serum concentration was 16.6±1.5 ng/ml. Serum rhRLX was not detected in any of the rats administered vehicle instead of rhRLX except (inexplicably) for one animal with a value of 0.84 ng/ml.

Example 3

Systemic Relaxin Administration Stimulates Angiogenic/Vasodilatory Cytokine Expression and Vesselformation in a Rat Myocardial Infarct Model.

Female Sprague Dawley rats, approximately 12-weeks of age were used. Rats were anesthetized by intraperitoneal (i.p.) injection of up to 1 ml/kg ketamine/medetomidine (6:4). Following exteriorization of the heart, the left coronary artery was ligated near its origin with a silk suture. In sham surgery control animals, the suture was placed superficially into the muscle adjacent to the coronary artery. Post-closure EKG's were monitored for S–T segment elevation in LCAL animals to confirm the outcome of ligation. Immediately following cardiac surgery, a primed mini-osmotic pump containing relaxin or vehicle (20 mM acetate, pH 5.0) was aseptically implanted into a subcutaneous (s.c.) pocket on the dorsal interscapular region. Vehicle or relaxin (0.1 mg/kg/day) was delivered as a continuous s.c. infusion for 7 or 21 days to either sham or LCAL animals. Animals were terminated on day 7 or 21, and the peri-infarct regions anterior to the scar in the left ventricle, or equivalent sites on sham surgery animals were harvested.

The left coronary artery ligation (LCAL) model of myocardial ischemia in the rat (Selye et al. (1960) *Angiology* 11:398–407) caused profound, acute damage, involving up to 50% of the left ventricular free wall. Following systemic relaxin treatment, using rhRLX, tissue RNA was examined at 7 and 21 days post-infarction for persistent changes in VEGF and bFGF. Cells in the immediate margins surrounding the infarct were sampled to assess angiogenic cytokine expression, using quantitative RT-PCR analysis. Oligonucleotide primers and TaqMan probes, shown in Table 8, were purchased from BioSource International Inc. (Camarillo, Calif.), or PE Applied Biosystems for use with the ABI Prism[7] 7700 Sequence Detection System (quantitative PCR) (PE Applied Biosystems).

TABLE 8

| Transcript | Sequence |
|---|---|
| Rat $VEGF_{164}$ Probe- | 'FAM'-TTGCAAGGCGAGGCAGCTTGAGT (SEQ ID NO:1) |
| Rat $VEGF_{164}$-Sense | TTCCTGCAAAAACACAGACTCG (SEQ ID NO:2) |
| Rat $VEGF_{164}$-α-sense | GGTCTTTCCGGTGAGAGGTCTA (SEQ ID NO:3) |
| Rat $VEGF_{120}$-Probe- | 'FAM'-CCAGAAAAATGTGACAAGCCA (SEQ ID NO:4) |
| Rat $VEGF_{120}$-Sense | GCAGATGTGAATGCAGACCAAA (SEQ ID NO:5) |
| Rat $VEGF_{120}$-α-sense | CTAGTTCCCGAAACCCTGAGG (SEQ ID NO:6) |
| Rat bFGF Probe-Sense | 'FAM'-TGTCCATCAAGGGAGTGTGTGCGAA (SQ ID NO:7) |
| Rat bFGF-Sense | CTACAGCTCCAAGCAGAAGAGAGA (SEQ ID NO:8) |
| Rat bFGF-α-sense | AGTTATTGGACTCCAGGCGTTC (SEQ ID NO:9) |
| Rat GAPDH Probe-Sense | 'TET'-ACCCATCACCATCTTCCAGGAGCG (SEQ ID NO:10) |
| Rat GAPDH-Sense | TTCAATGGCACAGTCAAGGC (SEQ ID NO:11) |
| Rat GAPDH-α-sense | TCACCCCATTTGATGTTAGCG (SEQ ID NO:12) |
| hu $VEGF_{165}$Probe-Sense | 'TET'-AGCAAGACAAGAAAATCCCTGTGGGCC (SEQ ID NO:13) |
| hu $VEGF_{165}$-Sense | CCAGCACATAGGAGAGATGAGC (SEQ ID NO:14) |
| hu $VEGF_{165}$-α-sense | GGAACATTTACACGTCTGCGG (SEQ ID NO:15) |
| hu $VEGF_{121}$Probe-Sense | 'FAM'-AGAAAAATGTGACAAGCCGAGGCGG (SEQ ID NO:16) |
| hu $VEGF_{121}$-Sense | CCACTGAGGAGTCCAACATCAC (SEQ ID NO:17) |
| hu $VEGF_{121}$-α-sense | AGATCTGGTTCCCGAAACCCT (SEQ ID NO:18) |
| hu bFGF Probe-Sense | 'FAM'-TATGTGGCACTGAAACGAACTGGGC (SEQ ID NO:19) |
| hu bFGF-Sense | GAAGGAAGATGGAAGATTACTGGC (SEQ ID NO:20) |
| hu bFGF-α-sense | TTCTGCCCAGGTCCTGTTTT (SEQ ID NO:21) |
| hu HGF-Sense | TGGACTTCCATTCACTTGCAAGGC (SEQ ID NO:22) |
| hu HGF-α-sense | TGTAGGTCTTTACCCCGATAGCTC (SEQ ID NO:23) |
| hu GAPDH Probe-Sense | 'JOE'-CAAGCTTCCCGTTCTCAGCC (SEQ ID NO:24) |
| hu GAPDH-Sense | GAAGGTGAAGGTCGGAGTC (SEQ ID NO:25) |
| hu GAPDH-α-sense | GAAGATGGTGATGGGATTTC (SEQ ID NO:26) |

Oligonucleotides were designed to rat or human bFGF, human VEGF165 amino acid or 121 amino acid isoforms, and their respective rat homologues (VEGF$_{164}$ and VEGF$_{120}$), and human HGF (for use with the PE Applied Biosystems "GeneAmp PCR System 9600"). Rat and human GAPDH primers and probes were purchased from Bio-Source International Inc. and PE Applied Biosystems, respectively. Tissue samples and monolayer cells were suspended in RNA STAT-60 (Tel-Test, Inc., Friendswood, Tex.) and processed following vendor instructions. Reverse transcription-polymerase chain reaction (RT-PCR) was performed using either rat or human total RNA as template. 150 ng of total RNA was used for the analysis of VEGF, bFGF and HGF mRNA expression; 10 ng of total RNA was used for GAPDH mRNA expression. Reverse transcription-polymerase chain reaction (RT-PCR) reagents were purchased from PE Biosystems (Foster City, Calif.).

Figure 5:
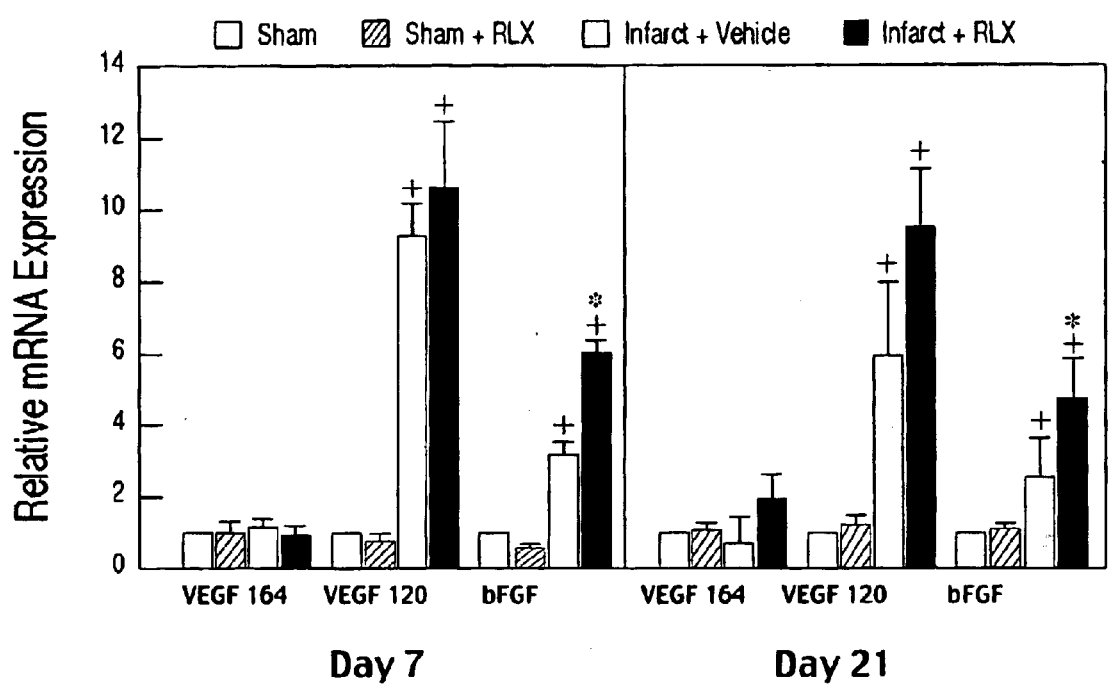
FIG. 5 is a graph depicting real-time quantitative reverse transcription-polymerase chain reaction (RT-PCR) analysis of expression of the rat $VEGF_{164}$ and $VEGF_{120}$ isoforms and rat bFGF in the pen-infarct area of rat hearts post-myocardial infarction.

The results are shown in FIG. 5. RNA was extracted from peri-infarct regions of rat hearts following LCAL or an analogous area of sham hearts. Animals were treated with either vehicle or relaxin (0.1 mg/kg/day) for either 7 or 21 days prior to sacrifice. Primer/probe sets were used to generate RT-PCR product specific for rat VEGF 164 aa (amino acid) and 120 aa isoforms, and rat bFGF. VEGF and bFGF expression levels are graphed relative to GAPDH transcript levels. Data are shown as means±SEM, where n=3 per treatment group; + indicates significantly different from sham; *p<0.05 compared to vehicle-treated infarct group; 1p<0.05 compared to shams, by Student-Newman-Keuls test.

These results demonstrate that mRNA levels of both VEGF$_{120}$ and bFGF were significantly (p<0.05) elevated in the infarct margins from animals 7 days following infarction, as compared to an analogous area from hearts subject to sham surgery. At day 21, VEGF$_{120}$ and bFGF mRNA levels remained elevated in peri-infarct areas compared to shams (p<0.05). Unexpectedly the level of VEGF$_{164}$ mRNA expression from peri-infarct tissue was not significantly different from the sham group at either time point. Absolute baseline levels of VEGF$_{164}$ mRNA transcripts, per microgram of total RNA, were approximately 10-fold greater than those of either the VEGF$_{120}$ isoform or those of bFGF in sham surgery hearts.

Systemic relaxin administration to infarcted animals caused a significant 2-fold increase in peri-infarct bFGF expression at both 7 and 21 days, compared to vehicle-treated infarcted hearts (p<0.05). At day 7, no changes in relative expression of either VEGF isoform were observed in the peri-infarct regions following relaxin treatment compared to vehicle treated hearts. At day 21 however, relative levels of VEGF$_{164}$ and VEGF$_{120}$ transcripts in relaxin treated hearts showed a trend towards an increase, compared to vehicle treated hearts. Relaxin administration to sham surgery animals had no effect on VEGF or bFGF mRNA expression.

Immunohistochemical analysis of the peri-infarct area of the heart was performed as follows. Transverse sections from paraffin embedded hearts were obtained at 3 levels. Sections were stained with H&E to assess neovascularization. Slides of heart sections were deparaffinized in xylene and washed with ethanol. Slides were then rinsed in sterile double distilled water before proceeding with antigen retrieval, as recommended by the antibody vendor (Biogenex). Sections were incubated for 30 minutes in 1.5% normal goat blocking serum (Biogenex, San Ramon, Calif.) and washed three times for 5 minutes each with PBS. Sections were then incubated with a monoclonal antibody against VEGF (VEGF-C1), or a polyclonal antibody against bFGF (FGF-2–147) (both at 5 µg/ml), before washing with PBS. Primary, and anti-goat or anti-rabbit secondary antibodies were purchased from Santa Cruz Biotechnology (Santa Cruz, Calif.). Sections were then incubated in multilink, a biotinylated goat anti-immunoglobulin for use with mouse, rabbit, guinea pig and rat primary antibodies (Biogenex) for 30 minutes at room temperature, followed by washing twice for 10 minutes each with PBS. Sections were labeled with peroxidase conjugated streptavidin for 20 minutes before finally washing twice for 5 minutes with PBS and air-drying). Animals were treated with either vehicle or relaxin (0.1 mg/kg/day) for either 7 or 21 days prior to sacrifice. Transverse slices were obtained along an axis midway between the apex and base of the heart. Sections were then stained with an antibody against rat bFGF.

The results indicated that bFGF was detectable as diffuse staining in cardiomyocytes in sham surgery hearts. Following infarction, bFGF staining intensified in the peri-infarct regions at both 7 and 21 days. Upon relaxin treatment, bFGF staining in the infarct margins intensified. When scored in blinded fashion, relaxin-treated hearts showed more intense peri-infarct bFGF staining than vehicle-treated hearts at both 7 and 21 days, with peak staining intensity at day 7 following treatment with relaxin. Both cardiomyocytes, identified by colocalization with desmin, and fibroblasts, which stained with vimentin, showed enhanced bFGF expression.

Sections of the left ventricle from rats with sham surgery showed homogenous, diffuse staining for VEGF protein in cardiomyocytes, similar to staining for bFGF. Following infarction, intense VEGF staining occurred in the peri-infarct regions at 7 and 21 days in both myocytes and fibroblasts. No differences in intensity of VEGF staining between relaxin and vehicle-treated hearts were detected by this method.

The number of venules, arterioles and capillaries in the infarct and peri-infarct areas of the left ventricle were quantified by counting individual vessels on H & E (hematoxylin and eosin) stained sections. Numbers of venules, arterioles and capillaries were determined by counting in the area of the infarct, and in the right and left junction areas between the infarcted free wall and viable myocardium. Quantitation of venules and arterioles were obtained as total number of vessels in the entire area in each of 3 H&E stained transverse sections of the heart, i.e. apical, basal and midway between apical and basal levels. Quantitation was performed by a histopathologist blinded to the treatment groups. Venules comprised the observed increases in numbers of collateral vessels post-infarction. All veins counted in high dry fields were summed to yield vessel number per level. Three levels (apical, basal, and middle) were summed for each animal to yield total number of veins. N=4–5 animals per treatment group. Systemic relaxin administration was associated with an increase in the number of venules present at day 7 from 113±28 in the infarct region in the acetate group to 163±8 in the similar region in the relaxin group. This increase was significant at day 21 (p<0.05), as the vessel number increase from 156±15 in the acetate group to 209±13 in the relaxin group. Relaxin administration did not alter the number of vessels in an analogous area of the left ventricle following sham surgery.

To further characterize the response of cardiac cells to relaxin, primary cultures of human fetal cardiac cells were assessed for the ability to bind $^{32}$P-relaxin. Primary human cardiac cells were purchased from Clonetics-BioWhittaker (San Diego, Calif.). Cells were derived from two 19 week-old, and one 20 week old male fetus. Cells were grown in Smooth Muscle Basal Medium (SmBM) supplemented with bFGF, EGF, insulin, gentamycin, amphoteracin B and 5% fetal calf serum, as prescribed by the vendor (media and supplements from Clonetics) at 37° C., 5% $CO_2$. Cardiac cells were seeded in 35 mm wells at $2.5 \times 10^5$ cells per well 24 hr prior to competitive binding assay. Total and specific binding was then measured. Percent specific binding was calculated as (total binding—nonspecific binding)÷(total binding)×100. Human fetal cardiac cells (obtained from three donors, 19 to 20 weeks of age) in culture were treated with 100 μM $^{32}$P-labeled relaxin for 2 hr at room temperature with or without a 1000-fold excess of unlabeled relaxin. Binding to rat neonatal cardiac cells is provided for comparison. Each donor culture was examined in triplicate. Specific, displaceable binding ranging from 40% to 55% was demonstrated on human cardiac cells from multiple fetal donors (19 and 20 weeks gestational age). Staining of the monolayer of fetal cardiac cells showed 100% staining for vimentin. Approximately 10–20% of the cells stained with both desmin and vimentin, suggesting the acquisition of a differentiated myocyte-like phenotype by a proportion of cells.

Figure 6:
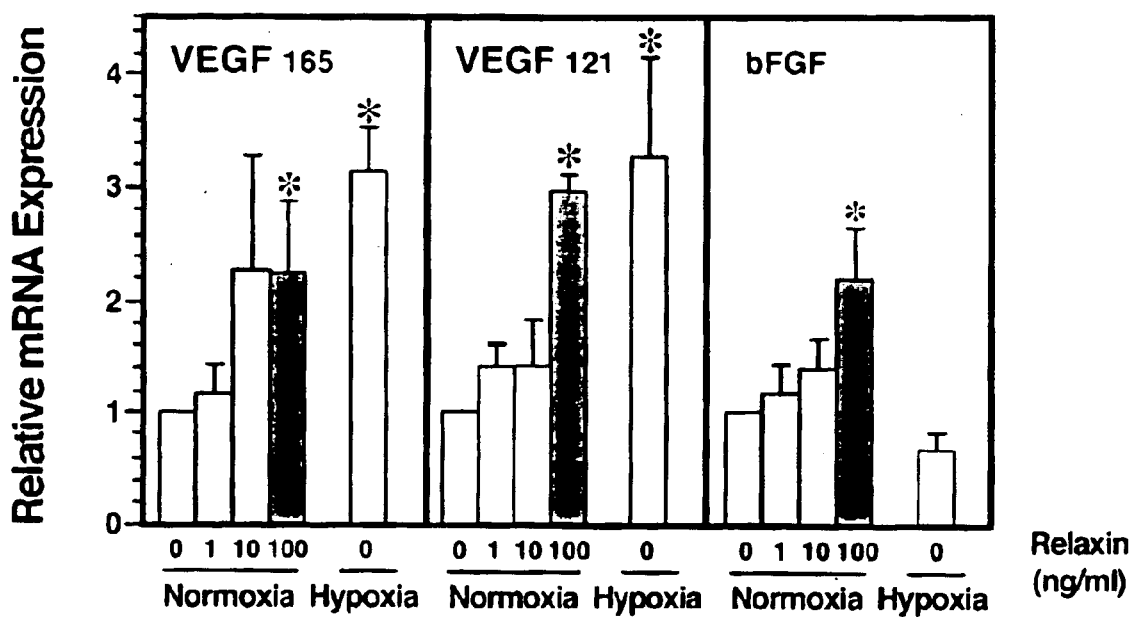
FIG. 6 is a graph depicting real-time quantitative RT-PCR of the human $VEGF_{165}$ and $VEGF_{121}$ isoforms and human bFGF following relaxin treatment in vitro.

To determine if the effects of relaxin observed in the rat were also seen in human cells, total RNA from cardiac cells was extracted following treatment of cells with 1, 10, and 100 ng/ml relaxin for 24 hours. The results are shown in FIG. 6. Human cardiac cells were cultured for 24 hours either without or with relaxin (1–100 ng/ml). Untreated cells were incubated for the same 24 hour period under hypoxic (2% $O_2$) conditions. Using 150 ng of total RNA for human VEGF and bFGF transcripts and 10 ng of total RNA for GAPDH transcripts, primer/probe sets were used to generate RT-PCR products for human VEGF 165aa and 121aa isoforns and human bFGF. Data were analyzed using Sequence Detector v1.6.3 software (Applied Biosystems/PE). VEGF and bFGF expression levels are graphed relative to GAPDH transcript levels. Data are shown as means±SEM, where n=3 per treatment group; *p<0.05; Student-Newman-Keuls test. Relaxin induced dose-related increases in the expression of transcripts of $VEGF_{165}$, $VEGF_{121}$ and bFGF, as shown in FIG. 6. $VEGF_{165}$ and VEGF121 mRNA showed maximum 2.3-fold and 3-fold increases in expression over untreated controls at 100 ng/ml doses of relaxin (p<0.05). Basic FGF expression also demonstrated a dose-dependant increase, reaching a maximum elevation of 2.2-fold over baseline at the 100 ng/ml dose (p<0.05). Absolute baseline levels of bFGF mRNA transcripts expressed by these cells were approximately 2-fold greater than those of either the $VEGF_{121}$ or the $VEGF_{165}$ isoforms. Total RNA from cells incubated under hypoxic conditions was analyzed as a positive control for the stimulation of VEGF isoforms. As predicted, mRNA transcript levels for both VEGF isoforms increased 220% over untreated control levels following 24 hr exposure to hypoxia, as shown in FIG. 6. bFGF expression was not induced by hypoxia. Transcripts for human HGF, another potent angiogenic factor (Morishita et al. (1999) *Hypertension* 33:1379–1384) showed no difference in expression between untreated and relaxin treated cells. Relaxin had no effect on cellular proliferation, as assessed by $^3$H-thymidine incorporation, on cellular morphology, or on desmin or vimentin staining patterns.

Consistent with RT-PCR data, relaxin stimulated a small but significant dose-related increase in levels of VEGF protein secreted by human cardiac. Cells were seeded in 35 mm wells at $2.5 \times 10^5$ cells per well 24 hours prior to treatment with relaxin. Cells were washed twice with SmBM (no supplements) and incubated for 2 hr with SmBM treatment medium (containing 400 pg/ml bFGF, gentamycin, amphoteracin B, and 2% fetal calf serum) at 37° C., 5% $CO_2$. The medium was then replaced with SmBM treatment medium without relaxin or with concentrations of relaxin from 0.1 ng/ml to 100 ng/ml. Cells were then incubated for 24 hr (37° C., 5% $CO_2$). Relaxin stimulated significant dose-related increases in VEGF secretion at all doses, with maximum induction to 155% over control levels at the 100 ng/ml dose.

Human cardiac cell cultures untreated or treated for 24 hr with 1, 10, and 100 ng/ml of relaxin were analyzed for VEGF and bFGF protein expression by immunocytochemistry. Human cardiac cells were seeded in two chamber slides at 150,000 cells per chamber 24 hours prior to treatment with relaxin. Cells were incubated without or with 10 or 100 ng/ml relaxin for 24 hours. Cells were washed with PBS and fixed with sequential treatment of 4% paraformaldehyde for 10 minutes, ice-cold acetone for 1 minute and ice-cold methanol for 1 minute before air-drying. Slides were then processed as outlined for rat heart sections with the additional use of monoclonal antibodies against vimentin or desmin (Santa Cruz Biotechnology). Cells being analyzed for bFGF expression were stained using the protocol outlined by Vector Laboratories "Vectastain Elite ABC" kit (Vector Labs.), the only deviation from the standard protocol being a 1 hour instead of a 30 minutes primary antibody incubation step. Untreated cells stained diffusely and uniformly for bFGF. Nearly 100% of all cells stained more intensely for bFGF expression following treatment with 10 and 100 ng/ml of relaxin for 24 hours.

Example 4

Systemic Administration of rhRLXstimulates Ischemic Wound Healing in Rats

The effect of rhRLX on normal and ischemic wound healing in two rat models of dermal wound healing was evaluated. RhRLX in vehicle, or vehicle alone, was delivered by subcutaneous infusion to Sprague-Dawley rats using an implanted ALZET7 osmotic pump (Alza Corp., Mountain View, Calif.).

In the first model, Hunt-Schilling wound chambers were implanted subcutaneously at either the shoulder or the hip region. The fluid and cells contained within each wound chamber were collected on day 18 for analysis of VEGF protein and mRNA. VEGF protein was detected and measured using ELISA. VEGF-encoding mRNA was detected using Northern blotting and RT-PCR. The granulation tissue within the wound chambers was collected for histological and immunohistochemical evaluation.

In the second model, a standardized ischemic, H-shaped, double flap wound was made on the back region. The area of surface necrosis was measured on day 14 and day 21.

In the wound chamber model, VEGF and bFGF mRNA were increased by 31% and 59%, respectively, in the rhRLX-treated rats compared to vehicle-treated rats, at both the shoulder and hip region. The amount of granulation tissue (vehicle, 182 mg; rhRLX, 255 mg; p<0.05), the number of capillaries, and the amount of extracellular matrix deposition within the wound chambers in the hip region were all increased by rhRLX treatment. There was little or no effect of rhRLX treatment on tissue weight (vehicle, 261 mg; rhRLX, 283 mg) or histological appearance of tissue from wound chambers in the shoulder region.

In the ischemic, H-shaped flap model, rhRLX treatment reduced the surface necrotic area in the flap region, compared to vehicle treatment (vehicle, 195 $mm^2$; rhRLX, 123 $mm^2$).

These results indicate that systemic administration of rhRLX stimulates wound healing in ischemic regions through its pro-angiogenic and vasodilatory properties.

Example 5

Relaxin Reduces Hypoxia-Induced Pulmonary Hypertension

Protocols

Animals and Reagents

Outbred 6-week-old Sprague-Dawley rats, 200–220 g body weight, were obtained from Hilltop Laboratories, Scottdale, Pa. Recombinant human relaxin (rhRlx) (5.0 mg/ml in 20 mM sodium acetate, pH5.0) and vehicle (20 mM acetate, pH5.0) were provided by Connetics Corporation (Palo Alto, Calif.). Miniosmotic pumps were purchased from Alza Corporation (Model 2002, Alza Corp., Palo Alto, Calif.).

Groups and preparation of infusion pumps

Mini osmotic pumps were filled to deliver rhRlx at 0.24 mg/kg/day (low rhRlx), 0.05 mg/kg/day rRlx (hi rhRlx), or vehicle alone. Osmotic pumps were inserted subcutaneously in rats under a combination of ketamine and xylazine anaesthesia. The area around the back of the neck was shaved, cleaned with alcohol, and a small incision made for pump insertion. Incision was closed with surgical staples. After the animals were fully conscious they were randomly assigned to either hypoxic exposure or room air. Rats were subjected to either air or hypoxia, as described below. There were three groups of rats subjected to air: vehicle-treated (veh-air), 0.05 mg/kg/day rhRlx (low rhRlx-air), and 0.24 mg/kg/day rhRlx (hi rhRlx-air). There were three groups subjected to hypoxia: vehicle (veh-hyp), 0.05 mg/kg/day rhRlx (low rhRlx-hyp), and 0.24 mg/kg/day rhRlx (hi rhRlx-hyp).

Hypoxic Exposure and Hemodynamic Measurements

Rats were exposed to hypoxia (10% $O_2$, 90% $N_2$) at ambient pressure (Kerr et al., 1987) for 10 days, control groups were exposed to room air in the same room. Hypoxic animals were fed standard rat chow and water. Age-matched control groups were weight-matched by feeding the amount of food consumed by the rats in the hypoxic groups. At the end of the test period, mean right ventricular pressure (RVP) was measured in rats anaesthetized with an intraperitoneal injection of 50 mg/kg pentobarbital sodium. The portal vein was then cut for hematocrit measurement (Hct) and blood sampling, and the ratio of the right ventricle to left ventricle plus septum measured [RV/(LV+S)] (Kerr et al., 1987). To determine the effect of acute administration of rhRlx on pulmonary artery pressure, four 10-day hypoxic rats were anaesthetized, as previously described, and RVP monitored for 1 hr following administration of a bolus dose of 2 $\mu$g rhRlx in 0.2 ml total volume, followed by an infusion of 2 $\mu$g rhRlx in 0.2 ml, given over 10 min.

Biochemical Assays

The pulmonary artery trunk, right and left extrapulmonary branches were removed en bloc, cleaned of surrounding tissue, and weighed. The left lung was and excised and the entire hilar artery dissected from parenchyma and weighed (Tozzi et al. (1994) Am. J. Respir. Crit. Care Med. 149:1316–1326). Segments were hydrolyzed, and total hydroxyproline and protein determined (Poiani et al. (1990) Circ. Res. 66:968–978). Approximately 3 cc of whole blood was centrifuged, serum aspirated, and sample frozen at −20° C. for determination of rRlx levels by ELISA assay.

Cell Culture

Aortic adventitial fibroblasts from normal adult Sprague/Dawley rats were explanted by carefully dissecting the adventitia away from the media and culturing 1 $mm^3$ pieces in Dulbecco's modified Eagles Medium (DMEM), plus 10% bovine fetal calf serum. When cultures were confluent, fibroblasts were dispersed with trypsin and passaged once prior to use in experiments. Fibroblasts were seeded at $10^5$ cells/$cm^2$ in DMEM+10% FBS in 48-well plates for experiments and assayed for collagen and fibronectin expression, as previously described (Unemori et al. (1996) J. Clin. Invest. 98:2739–2745). Briefly, fibroblasts were incubated with 1 ng/ml of recombinant human transforming growth factor-$\beta$ (TGF-$\beta$) (R & D Systems, Minneapolis, Minn.) in DMEM supplemented with 0.2% lactalbumin hydrolysate for 24 hours to stimulate extracellular matrix production. Half of the cultures were also treated simultaneously with 10 ng/ml of rhRlx. Proteins were biosynthetically labeled with $^3$H-proline (25 $\mu$Ci/ml) (Amersham Corp., Arlington Heights, Ill.), in the presence of ascorbate (50 $\mu$g/ml) and $\beta$-aminopropionitrile (80 $\mu$g/ml), and conditioned media collected 24 hours later. Media were electrophoresed on SDS-PAGE, and the density of collagen and fibronectin bands was determined by densitometric scanning using a digital imaging system (Alpha Innotech Corp, San Leandro, Calif.).

Relaxin ELISA

Levels of relaxin in serum were measured in a quantitative sandwich immunoassay, as previously described (Unemori et al. (1996) J. Clin. Invest. 98:2739–2745). The assay has been validated for use with rat serum, shows no detectable cross-reactivity with rat relaxin, and has a lower limit of detection of 20 pg/ml.

Statistics

Data were expressed as mean±SEM. Analysis was performed using one-way ANOVA followed by Tukey-Kramer multiple comparison testing using GraphPad InstatJ software and ANOVA with repeated measures (SAS).

Results

Animals

Survival was 100% in all groups. Body weights of the hypoxic and control groups at 10 days were not statistically different, as shown in Table 9.

TABLE 9

| Group | n | Body weight, grams | rRlx serum levels, ng/ml |
|---|---|---|---|
| Veh-hyp | 15 | 240 ± 2 | 0 |
| 1 mg-hyp | 15 | 242 ± 32 | 3.2 ± 0.4 |
| 5 mg-hyp | 10 | 246 ± 3 | 11.5 ± 2.5 |
| Veh-air | 15 | 244 ± 3 | 0 |
| 1 mg-air | 15 | 246 ± 2 | 2.9 ± 1.0 |
| 5 mg-air | 10 | 249 ± 4 | 9.9 ± 2.8 |

Serum levels of rhRlx on day 10 of exposure to either hypoxia or normoxia were 3.2±0.4 ng/ml (low rhRlx-air), 11.5±2.5 ng/ml (hi rhRlx-air), 2.9±1.0 ng/ml (low rhRlx-hyp), 9.9±1.0 ng/ml (hi rhRlx-hyp). Values were significantly higher in the hi rhRlx groups compared to the low rhRlx groups (p<0.05, n=8–16), and air and hyp groups were not significantly different. Serum levels attained were similar to levels observed in early pregnancy in rats (Sherwood (1994) Relaxin in The Physiology of Reproduction, E. Knobil and J. D. Neill, eds., Raven Press).

Hemodynamics

Figure 7:
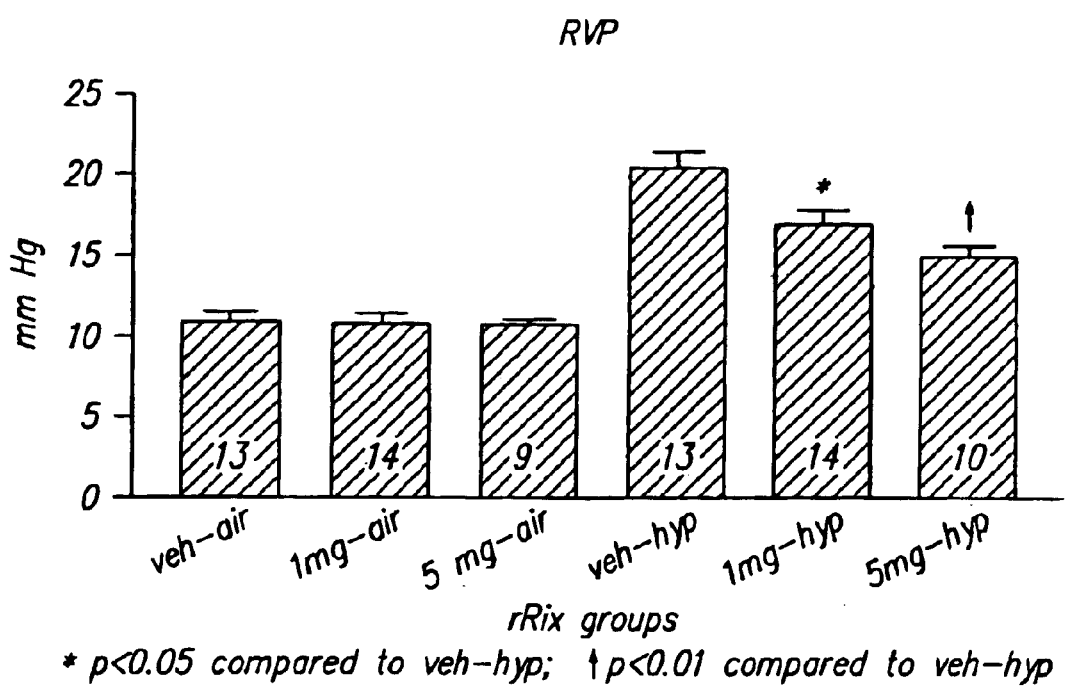
FIG. 7 is a graph depicting the effect of chronic administration of relaxin on right ventricular pressure (RVP) in rats kept under conditions of normoxia (air) or hypoxia.

After 10 days of hypoxia, mean RVP was significantly higher in the veh-hyp group than in the veh-air group. Chronic administration of rhRlx decreased RVP at both low ($p<0.05$) and high ($p<0.01$) doses compared to the veh-hyp group, as shown in FIG. 7. Mean RVP was not significantly different among air groups. RV/(LV+S) was significantly higher in the veh-hyp group compared to the veh-air group. Both the low rhRlx-hyp ($p<0.05$) and hi rhRlx-hyp ($p<0.01$) had RV/(LV+S) ratios that were significantly reduced compared to the veh-hyp group. RV/(LV+S) was similar in all air groups. Hct was not significantly different among hyp groups or among air groups; however, all hyp groups were significantly higher than air groups, as previously described (Barer et al. (1983) *J. Physiol.* (Lond.) 336:27–38).

Hydroxyproline and protein content of pulmonary arteries

Collagen content was assessed as micrograms of hydroxyproline per standard length of vessel, as shown in Table 10.

TABLE 10

| Group | Hydroxy-proline μg/vessel MPA | Hydroxy-proline μg/vessel Hilar | Protein mg/vessel MPA | Protein mg/vessel Hilar | n |
|---|---|---|---|---|---|
| Veh-hyp | 101.8 ± 1.9 | 48.4 ± 3.1 | 3.7 ± 0.2 | 1.8 ± 0.8 | 5 |
| 1 mg-hyp | 95.2 ± 3.6 | 41.0 ± 3.3 | 2.3 ± 0.2 | 0.90 ± 0.2 | 5 |
| 5 mg-hyp | 86.6 ± 6.0*↑ | 37.0 ± 5.0*↑ | 2.0 ± 0.4* | 0.75 ± 0.8* | 5 |
| Veh-air | 82.8 ± 4.0 | 35.8 ± 1.4 | 3.1 ± 0.3 | 0.94 ± 0.1 | 5 |
| 1 mg-air | 76.4 ± 4.0 | 38.0 ± 2.3 | 2.6 ± 0.2 | 0.78 ± 0.3 | 5 |
| 5 mg-air | 75.2 ± 4.0 | 33.5 ± 1.5 | 2.5 ± 0.3 | 1.1 ± 0.1 | 5 |

*$p \leq 0.05$ compared to veh-hyp; ↑ $p \geq 0.05$ compared to veh-air. MPA is main trunk pulmonary artery Hydroxyproline content of the main pulmonary arteries (MPA) and hilar vessels in the groups subjected to air was not significantly different from each other. Hydroxyproline content of the MPA and hilar vessels of rats in the veh-hyp group was significantly elevated over that in the veh-air group. Hydroxyproline content of the MPA and hilar vessels in the lo hRlx-hyp group was slightly decreased compared to the veh-hyp group, but the hi rhRlx-hyp group demonstrated significantly less hydroxyproline content than the veh-hyp group ($p<0.05$). Protein contents of the MPA and hilar vessels following treatment with the high dose of rhRlx were also significantly reduced compared to veh-hyp group ($p<0.05$).

Collagen and fibronectin etablexpression by adventitial fibroblasts

Rat aortic adventitial fibroblasts constitutively expressed interstitial collagens, as well as fibronectin. Treatment with TGF-β (20 ng/ml) increased expression of collagens to 484±67% of control levels. The addition of rhRlx (10 ng/ml) inhibited TGF-β-induced collagen over-expression by 21±5% ($p<0.05$). Fibronectin expression was also increased, to 360±5% of control levels, following TGF-β treatment. Relaxin treatment decreased TGF-β-induced over-expression by 28±6% ($p<0.05$).

Example 6

Relaxin Induces Vascular Endothelial Growth Factor Expression and Angiogenesis Selectively at Wound Sites Materials and Methods Reagents.

Recombinant human relaxin was manufactured by Genentech, Inc. (Lot #M3RD211, 1.5 mg/ml in 10 mM citrate, pH5.0) or Connetics Corporation (Lot 63601, 1.5 mg/ml in 10 mM acetate, pH5.5). Citrate or acetate buffer, respectively, were used as vehicle control in experiments. Recombinant human VEGF was purchased from R & D Systems (Minneapolis, Minn.).

Matrigel assay.

Animals were purchased from Harlan Sprague Dawley (Indianapolis, Ind.) and were housed according to NIH guidelines. Protocols were in compliance with institutional guidelines. Matrigel (Collaborative Biomedical, Bedford, Mass.) was mixed with relaxin to a final concentration of 100 ng/ml, or mixed with the identical volume of citrate buffer, on ice. 100 ml was injected subcutaneously into the flank of female Swiss Webster mice. At 11 days, the Matrigel plugs were harvested, fixed, and stained with H & E (hematoxylin and eosin) for assessment of new blood vessel ingrowth. Vessel growth was scored on a 0–5 scale: 0=no infiltration; 1=minor infiltration; 2 =3–5 cell layers infiltrating only margins of the plug; 3=5–10 cell layers infiltrating margins with some areas of deeper infiltration; <25% of plug infiltrated; 4=Many areas of deep cellular infiltration; 25–50% of plug infiltrated; 5=50–100% of plug infiltrated. Endothelial cells preferentially migrate into the basement membrane matrix.

Hunt-Schilling wound chamber assay.

Stainless steel mesh cylinders (0.9 cm×3.4 cm) fitted with silicone rubber plugs at both ends were autoclaved prior to implantation. Chambers were implanted into two separate subcutaneous pockets ("Site 1" on the shoulder and "Site 2" on the hip) on the backs of Sprague Dawley rats. At the same time, osmotic pumps were implanted in a subcutaneous pocket at site distal to that of the chambers. At 18 days, chambers were carefully dissected free from the interstitium, and fluid aspirated using an 18-gauge needle through the silicone plugs at the end of the cylinder, and immediately placed on ice. Cells suspended within the fluid were pelleted by centrifugation, and cells and fluid were separated. Total RNA was harvested using RNAzol (Tel-Test, Inc., Friendswood, Tex.), according to vendor instructions. Fluid was immediately frozen, and assayed at a later date for cyokine content.

RT-PCR analysis.

Oligonucleotide primers (see Table 8, above) were designed to amplify rat and human VEGF transcripts (primers did not distinguish isoforms), as well as those of the housekeeping gene, glyceraldehyde-6-phosphate dehydrogenase (GAPDH), using the PE Applied Biosystems GeneAmp PCR 9600 system. Primers were purchased from BioSource International (Camarillo, Calif.) and visualized using agarose gel electrophoresis.

Sense and anti-sense primers for use with the real time RT-PCR, ABI Prism 7700 Sequence Detection System were designed using the PrimerExpress version 1.0 software (PE Applied Biosystems, Inc.). Rat and human specific primer/probe sets included those for GAPDH, bFGF, the VEGF 164 aa or 120 aa rat isoforms, and their respective human homologues (VEGF 165 and VEGF 121). ABI PRISM specific primer/probes were purchased from BioSource International Inc. or PE Applied Biosystems.

RT-PCR was performed on 150 ng for the analysis of VEGF and bFGF mRNA expression. Ten nanograms of total RNA was used for GAPDH niRNA expression. PCR products using the ABI Prism 7700 Sequence Detection system (all reactions in a total volume of 50 ml) were generated using primer/probe annealing temperatures of 58° C. and 35 cycles of PCR. Data were analyzed using Sequence Detector v1.6.3 software (Applied Biosystems/PE).

3H-thymidine uptake.

Endothelial cells were derived from explant cultures of human neonatal foreskin and rat aorta. Primary human endothelial cells from umbilical vein, aorta, and lung were purchased from Clonetics-BioWhittaker Corporation (San Diego, Calif.) and cultured according to vendor instructions. $^3$H-thymidine uptake was performed, as previously described, in serum-free medium. Unemori et al. (1994) *Exp. Cell Res.* 21:166–171.

Cell culture.

THP-1 cells were obtained from the American Type Culture Collection (ATCC# TIB202), and grown in Iscove's medium supplemented with 10% fetal bovine serum and 2 mM L-glutamine. For experiments, THP-1 cells were cultured at $5 \times 10^5$ cells/ml in 24-well plates, treated and allowed to incubate for various times at 37° C. Conditioned media and cells were then collected, and cells removed by centrifugation at 500 g for 5 min. Media were stored at –80° C. until assayed.

ELISA.

VEGF protein was quantified in an ELISA kit purchased from R & D Systems (Minneapolis, Minn.). The lower limit of sensitivity of the assay was 10 pg/ml.

Statistical analysis.

Group comparisons were done using analysis of variance and the Student-Newman Keuls method for multiple comparisons. Pair-wise comparisons were done using paired t-test.

Results

Relaxin stimulates angiogenesis in vivo.

The ability of relaxin to induce new blood vessel growth in vivo was tested in the murine Matrigel system for assessing angiogenesis. Passaniti et al. (1992) *Lab. Invest.* 67:519–528. Relaxin was mixed with the Matrigel to a final concentration of 100 ng/ml before subcutaneous injection. At 10 days, Matrigel plugs were harvested, processed for histology, and H & E sections scored for vessel ingrowth in blinded fashion. Matrigel plugs containing vehicle alone (citrate or acetate buffer) had some degree of infiltration of cells, reflecting the ability of the Matrigel alone to stimulate a mild inflammatory reaction and consequent ingrowth of vessels. Vessels were identified morphologically as tubular structures that contained red blood cells. The average score of the control plugs was 2–3 on a scale of 0–5. In three separate studies, relaxin induced significantly more vessel ingrowth than did vehicle alone (p<0.05 vs vehicle control). Recombinant human VEGF (1 ng/ml), which was used as a positive control for angiogenesis in the assay, confirmed the ability of endothelial cells to respond to an angiogenic stimulus when mixed with the Matrigel and injected subcutaneously.

Relaxin was then assayed for the ability to induce proliferation of endothelial cells directly. Relaxin's potential mitogenic effect was tested on human primary umbilical vein, aortic, foreskin, and pulmonary endothelial cells, as well as rat aortic endothelial cells. Relaxin did not alter $^3$H-thymidine uptake in any of the endothelial cell types tested, unlike 10% serum, which was used as a positive control in these assays. Alterations in other aspects of endothelial cell phenotype that are believed to correlate with angiogenesis were also tested. Relaxin had no effect on collagen expression, judged by SDS-PAGE of $^3$H-proline-labeled cellular proteins; or metalloproteinase or tissue inhibitor of metalloproteinase-1 secretion, assessed by gelatin zymography. Relaxin had no effect on the ability of endothelial cells to invade the substrate or to form tube structures (i.e. in vitro capillaries) when cultured on a Type I collagen or Matrigel substrate, nor did it induce chemotaxis in vitro. Furthermore, binding of $^{32}$P-labelled relaxin to endothelial cells could not be detected. Therefore, relaxin had no apparent effect directly on endothelial cells.

Relaxin stimulates angiogenic cytokine expression in vivo.

Relaxin was administered systemically to rats using osmotic pumps. In order to assess relaxin's ability to modulate expression of angiogenic cytokines at wound sites, Hunt-Schilling wound chambers were used for fluid and inflammatory cell collection. Wound chambers were implanted subcutaneously at two sites, the shoulder and the hip, distal to the site of pump implantation. Fluid and cells were collected at a point (18 days) during the healing time course when endogenous angiogenic activity and the cellular source, macrophages, were known to be present. Total RNA was harvested from wound cells and analyzed by RT-PCR for VEGF transcripts. When analyzed on an agarose gel, there were two distinct bands comprising the amplified products, corresponding to the 121aa and 164aa, isoforms of VEGF. Expression of both isoforms appeared to be enhanced in relaxin-treated animals.

Quantitative real-time RT-PCR was then utilized for analysis of expression of the two isoforms of VEGF. Abundance of the transcripts was normalized to expression of the housekeeping gene, GAPDH (FIG. 8a). Expression of transcripts of both the VEGF 164 and VEGF 120 isoforms in control animals was higher in the hip wound chambers than the shoulder, but did not reach statistical significance (p=0.056 and 0.078, respectively). Relaxin administration upregulated expression of VEGF 164 mRNA in the anteriorly placed wound chamber (p<0.01) and was associated with a trend toward an increase in the chamber placed on the hip. VEGF 120 mRNA also showed trends toward increases at both sites following relaxin administration. A similar analysis was carried out for bFGF mRNA levels in wound cells (FIG. 8b). Baseline expression of bFGF mRNA transcripts was significantly higher in the wound chamber on the hip than on the shoulder, consistent with endogenous stimulation by the comparatively hypoxic environment of the posterior dermis. Relaxin induced a significant upregulation of bFGF transcripts in wound cells from both shoulder and hip chambers (both p<0.05).

Resident macrophages and immune cells from other non-wound sources were also harvested from vehicle- and relaxin-treated rats, and assayed for VEGF expression by RT-PCR. Alveolar macrophages or spleen cells had no detectable or a low level of VEGF expression which did not show an upregulation following relaxin treatment.

Relaxin induces rapid upregulation of VEGF mRNA in THP-1 cells.

Figure 9:
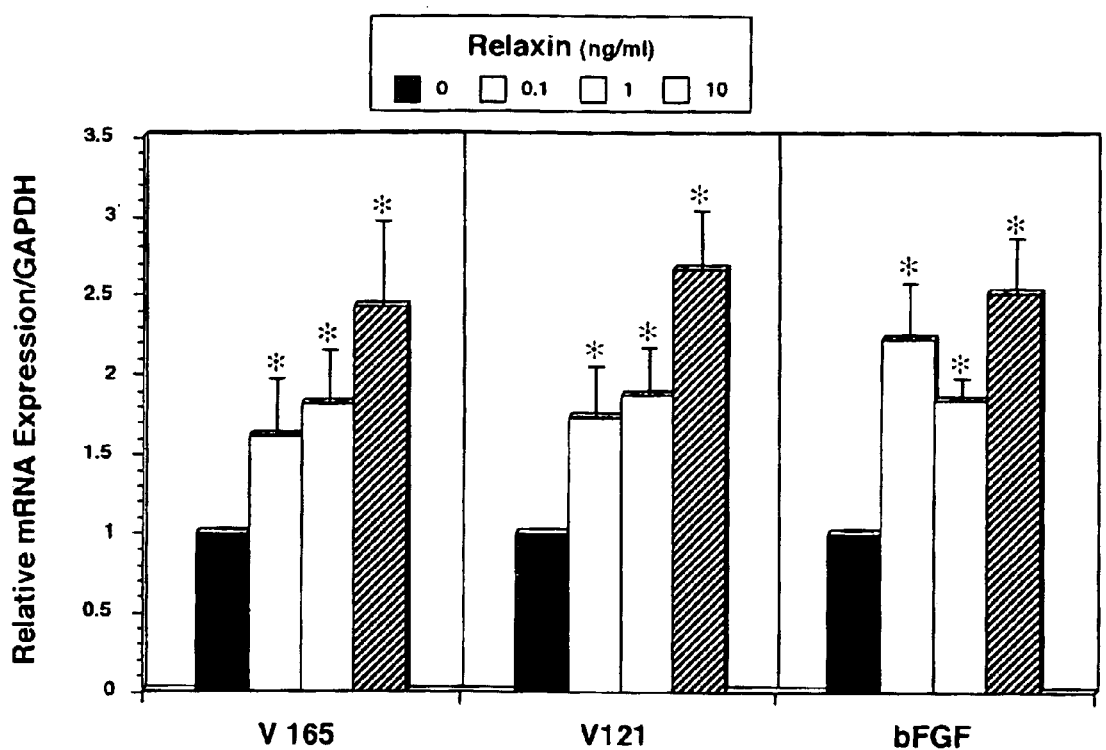
FIG. 9 is a graph depicting the effect of relaxin on VEGF (165- and 121-amino acid isoforms) and bFGF mRNA expression in THP-1 cells.
Figure 10:
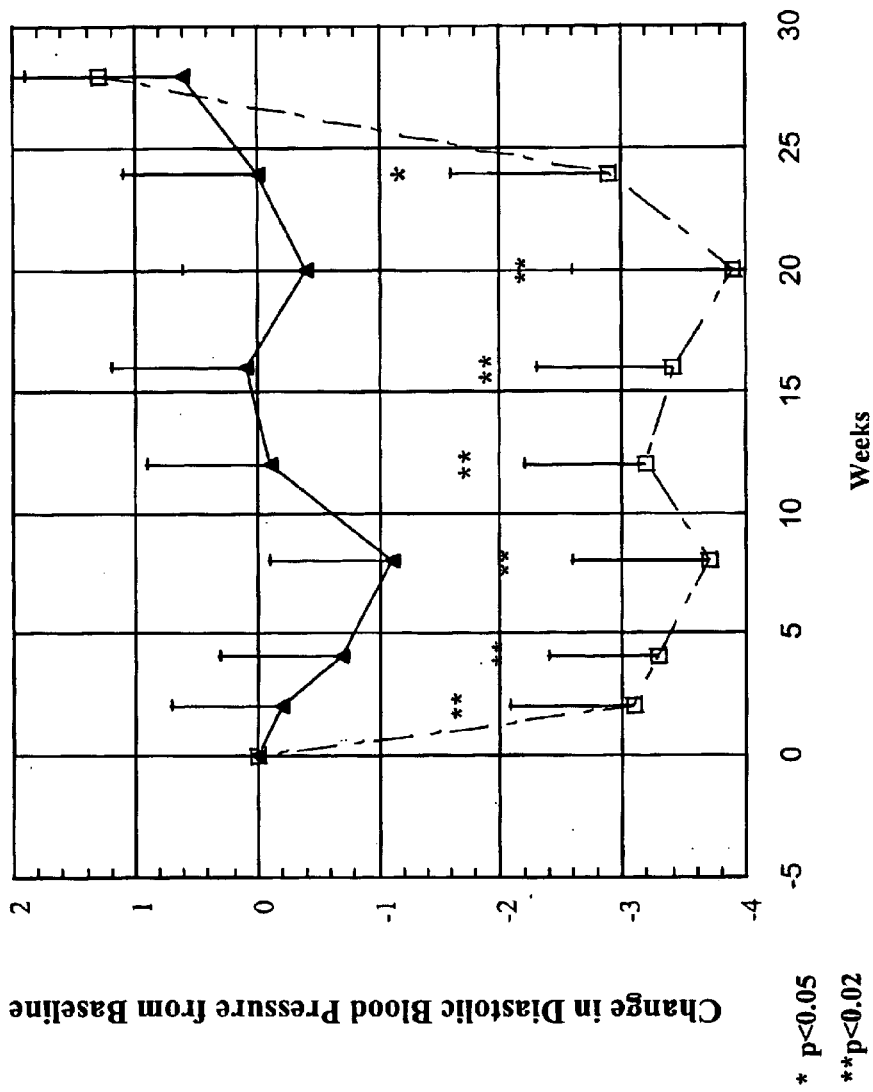
FIG. 10 is a graph depicting the change in diastolic blood pressure from baseline over a period of 26 weeks in humans treated with 25 μg/kg/day relaxin (solid triangles) or placebo (open squares) humans for 24 weeks.
Figure 11:
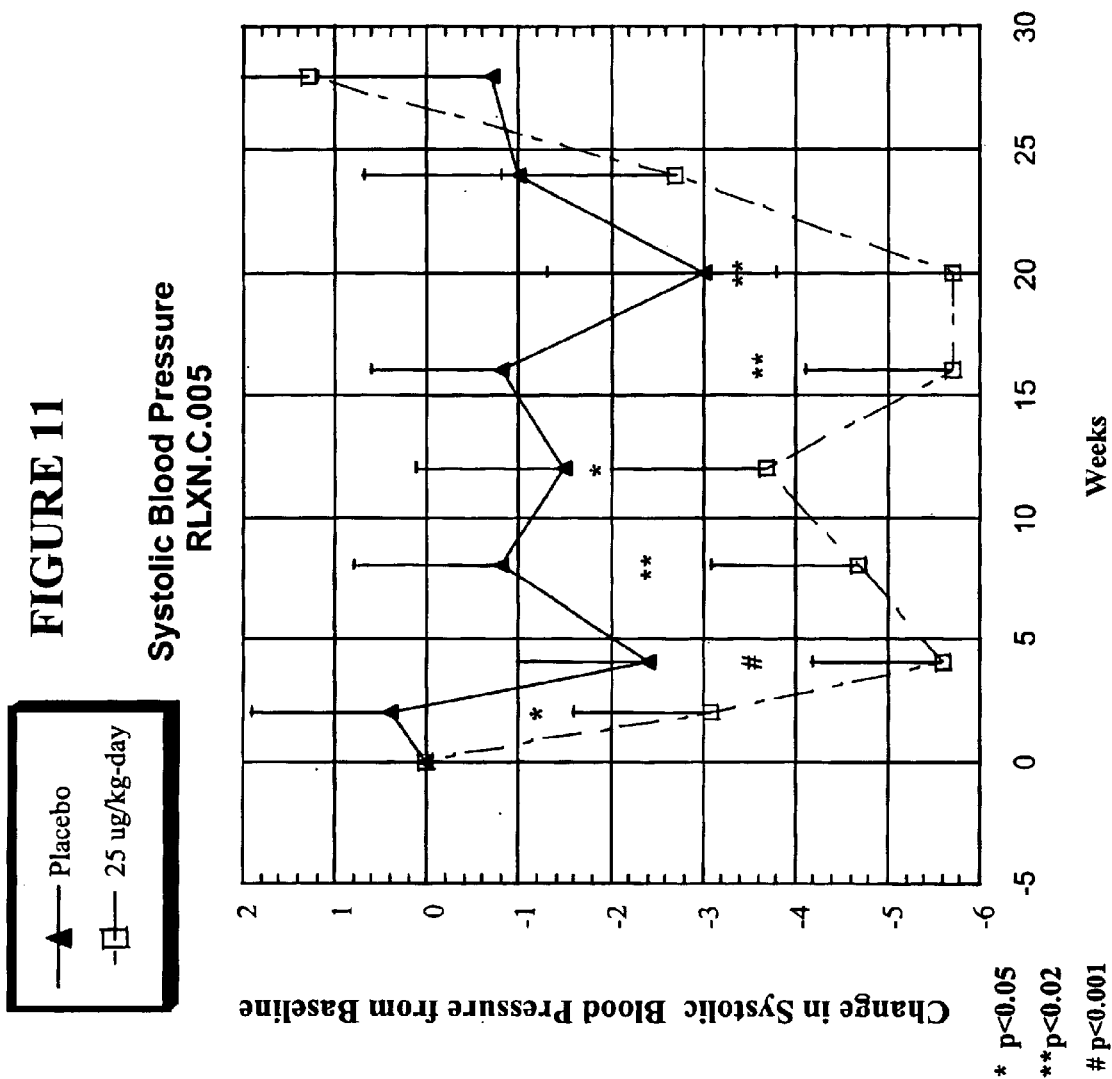
FIG. 11 is a graph depicting the change in systolic blood pressure from baseline over a period of 26 weeks in humans treated with 25 μg/kg/day relaxin (solid triangles) or placebo (open squares) humans for 24 weeks.
Figure 12:
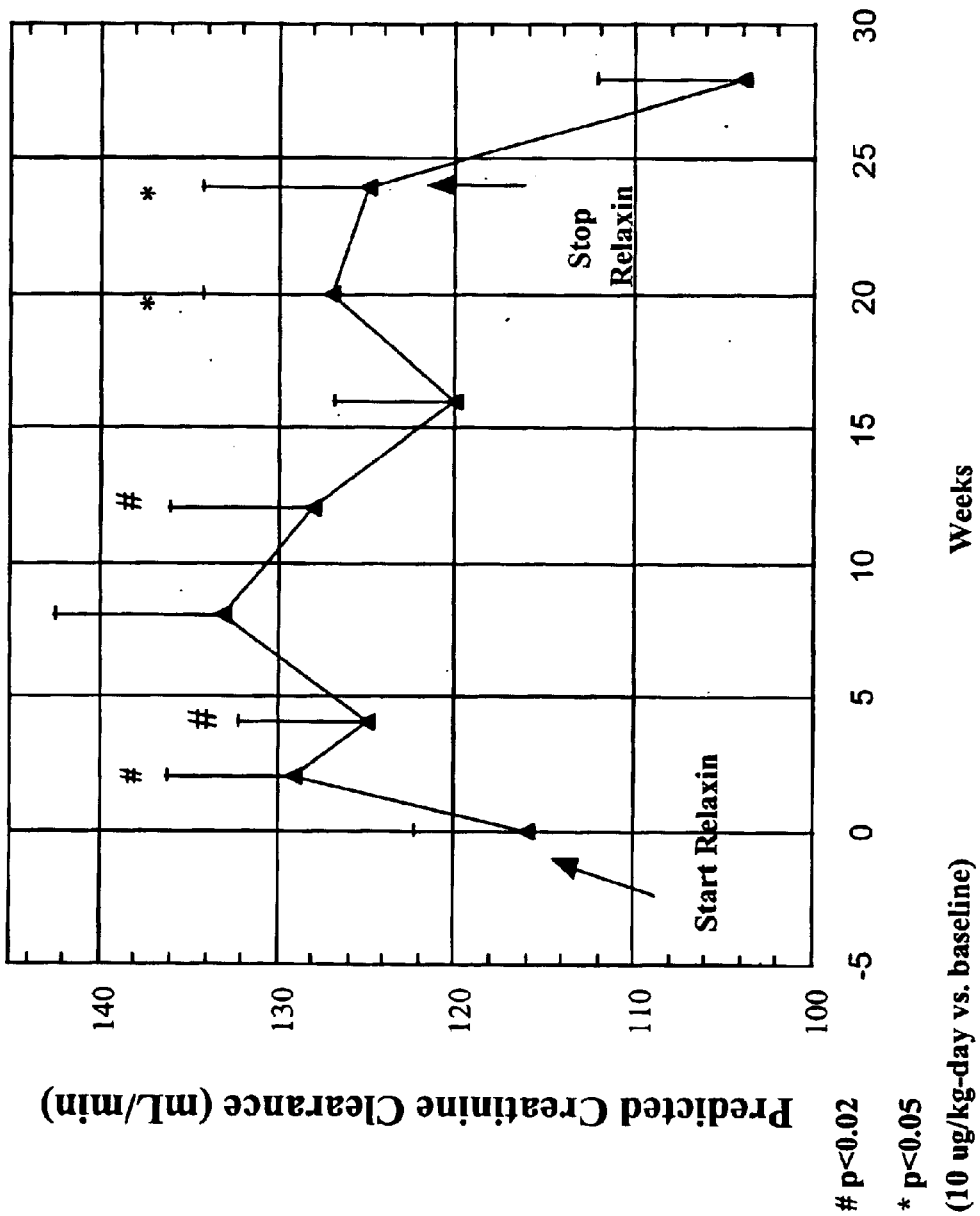
FIG. 12 is a graph depicting predicted creatinine clearance versus time in humans treated with 10 μg/kg/day relaxin.
Figure 13:
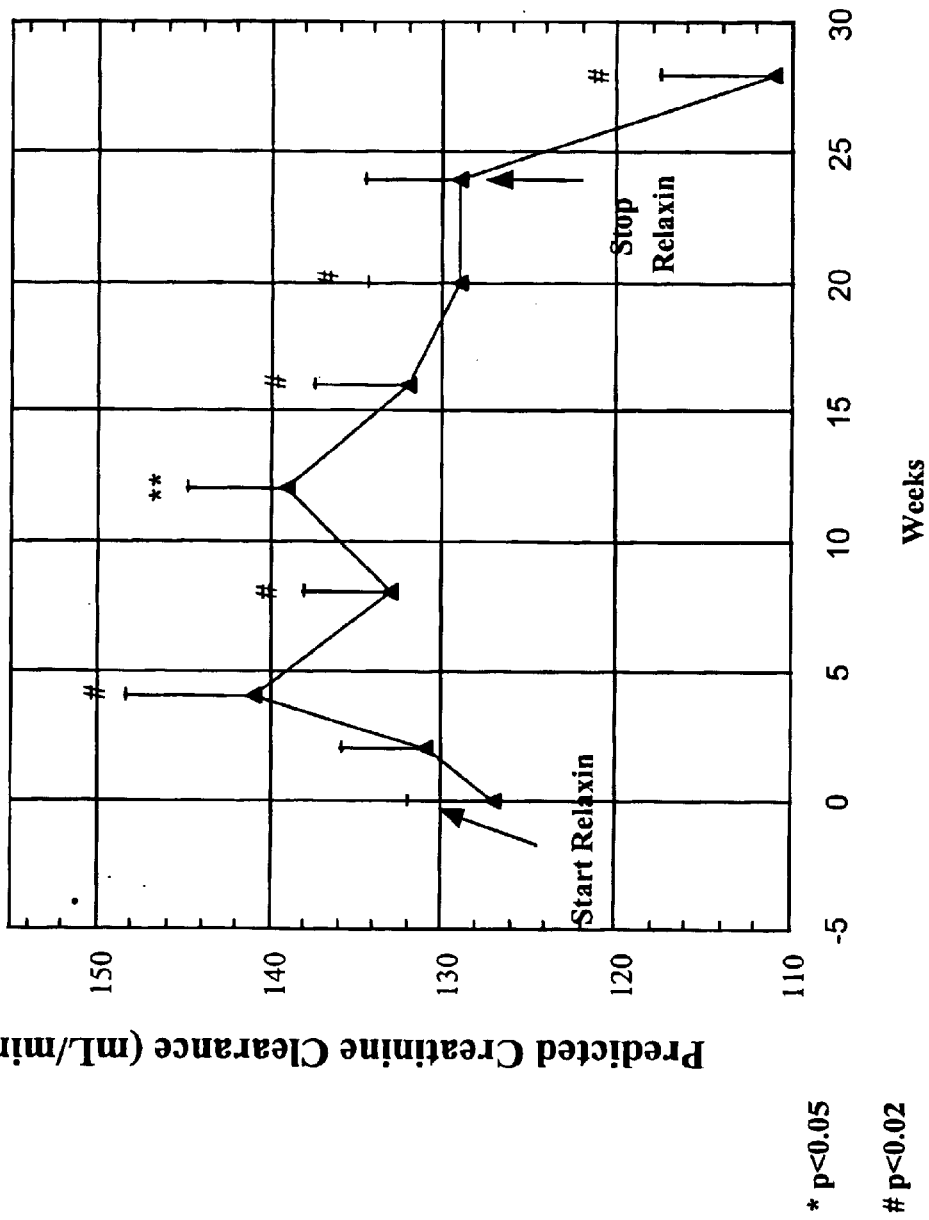
FIG. 13 is a graph depicting predicted creatinine clearance versus time in humans treated with 25 μg/kg/day relaxin.

Because macrophages are the inflammatory cells predominantly responsible for the angiogenic response that occurs during healing, a monocyte/macrophage cell line shown previously to bind relaxin with high affinity (THP-1) (Parsell et al. (1996) *J. Biol. Chem.* 271:27936–27941) was tested for relaxin inducibility of VEGF and bFGF. THP-1 cells were cultured in vitro, treated with relaxin (100 ng/ml) for 3 hours, and assayed for VEGF and bFGF mRNA induction. Transcripts for VEGF were specifically upregulated by relaxin treatment (FIG. 9). In order to determine whether the increase in VEGF mRNA observed following short-term relaxin treatment was reflected by an elevation in secreted VEGF protein, THP-1 cells were treated with relaxin (0.01–100 ng/ml) for 24 h, the conditioned media collected, and VEGF content in the media quantified by ELISA. Relaxin induced VEGF protein secretion in a dose-dependent manner, to approximately 150%, with a threshold relaxin concentration of 0.2–1.0 ng/ml required for stimulation. Relaxin caused no observable morphological changes, such as adherence to plastic or aggregation, nor did it influence $^3$H-thymidine uptake, or metalloproteinase expression patterns.

Example 7

Effect of Relaxin on Normal and Impaired Would Healing in Rats

To assess the effect of rhRlx treatment on granulation tissue formation in normal and ischemic wounds, Hunt-Schilling wound chambers were implanted subcutaneously in either the shoulder or the more hypoxic hip region of female Sprague Dawley rats (Charles River Laboratories, Mass.). The wound chambers, fine stainless steel mesh cylinders sealed with medical grade silicone, provide a defined dead space for granulation tissue formation. RhRlx or vehicle was administered continuously via an Alzet pump implanted subcutaneously. On day 18 after surgery, the granulation tissue contained within the chambers was harvested. The mean wet weight of granulation tissue (n=6) contained within the wound chambers from the hip region was lower than that in the wound chambers from shoulder region, presumably reflecting the more ischemic nature of the posterior site. Systemic administration of rhRlx was associated with a significant increase in the weight of granulation tissue in the wound chambers at the hip region (p<0.05), but not at the shoulder. The increase in granulation tissue in the chambers in the hip region was accompanied by an increase in bFGF, and VEGF expression in wounds cells and an increase in new blood vessel formation. These results indicate that rhRlx treatment selectively enhances granulation tissue formation in ischemic wounds by stimulating angiogenesis via the induction of VEGF and bFGF in wound cells.

To determine whether rhRlx would improve healing in this model of impaired healing, standardized full thickness (1.5 cm×1.5 cm) wounds were made on the back of db/db mice (Jackson Laboratories, Bar Harbor, Me.). Mice were treated continuously for 21 days with rhRlx via a subcutaneously implanted Alzet pump at a dose of either 0.1 mg/kg/day or 0.2 mg/kg/day. Wound areas were measured in the course of the study. Healing is presented as wound area on day 14 relative to the original size of the wound on day 0 and is calculated as: % of original wound area=[Area on day 14/area on day 0]×100. Systemic administration of rhRlx at a dose of 0.2 mg/kg/day significantly improved wound closure compared to that of animals treated with vehicle at 14 days. Wound closure was expressed as "% of original wound area." There were 8–20 animals per group. Wound closure was 91.4% in control group vs. 64% in the relaxin-treated group (p<0.05 by Student-Newman-Kuels test). The differences in the extent of wound healing were small among vehicle control and low dose of rhRlx treatment as well as PDGF (5 µg/wound/day for 5 days) treated mice.

At day 21-post surgery, the wounds were also excised and fixed in formalin prior to paraffin embedding. Sections from the middle of the wound were stained with Masson's trichrome and evaluated by two investigators. Wounds treated with rhRlx were covered by a thick, cellular and vascular granulation tissue. Wound treated with vehicle demonstrated a very thin layer of granulation tissue and little angiogenesis. Inflammatory cell accumulation was present at the wound edges.

Neovascularization is a key component of granulation tissue formation. New blood vessel formation is stimulated by a variety of growth factors including bFGF, and VEGF. Recently, we demonstrated relaxin's ability to induce both VEGF and bFGF in THP-a, a cell line of monocyte lineage, in vitro and in ischemic wound sites in vivo. Immunohistochemical staining of the midsection of full thickness wounds using polyclonal antibody to von Willebrand factor VIII-related antigen was used to identify new blood vessels in the wounds. Administration of rhRlx was associated with stronger positive staining in the wounds from rhRlx treated mice compared to the wounds of vehicle treated animals.

In the third animal model, a standard ischemic wound (H-shaped, 8 cm long and 2 cm wide) was created on the back region of rats. Perforating branches of the central vein were cut to ensure that the wound was ischemic. The resulting wound is then ischemic, but not completely necrotic. On day 14 and day 21, the surface necrosis was measured. RhRlx treatment (0.2 mg/kg via minipump) reduced the surface necrotic area in the flap region, compared to vehicle treatment (at day 14: vehicle 195 mm$^2$, rhRlx 123 mm$^2$; at day 21 vehicle 180 mm$^2$, rhRlx 103 mm$^2$). Immhunohistochemical staining on NO synthase indicates that systemic treatment of rhRlx enhances the expression of NO synthase on vascular endothelium.

Example 8

Relaxin Increases Kidney Function in Cyclosporine-treated Rats

Cyclosporine A (CsA) is used as an immunosuppressant to prevent or reduce the incidence of transplant rejection in transplant patients. A significant drawback to its use, however, is that nephrotoxicity is associated with its prolonged use. Studies were conducted to determine whether relaxin could ameliorate the untoward effects of CsA on kidney function.

Female Sprague-Dawley rats, 10–12 wks old (body weight 250 g) were treated with CsA 30 mg/kg/day by oral gavage (day 0–10). Relaxin (rhRlx) was administered via subcutaneous pumps at dose of either 0.1 mg/kg/day or 0.5 mg/kg/day for 10 days (day 0–10). On day B2 (baseline), Day 4, and Day 9, all rats were put into metabolic cages. The 24-hour urine volume was measured to calculate urine flow rate using the following formula:

Urine flow rate=24-hour urine volume/1440 minutes/body weight

Blood and urine were collected for creatinine measurement to calculate the GFR using the following formula:

Creatinine clearance=Urine creatinine in 24-hour volume/Serum creatinine per 1440 minutes Urine flow rate for CsA treated rats, and GFR (glomerular filtration rate) for CsA treated rats was measured, and the results indicated that CsA treatment decreases renal function. The results of relaxin treatment of normal and CsA-treated animals are shown in Tables 11 and 12, below. In this system, systemic treatment of rhRlx (0.5 mg/kg) to normal rats enhanced both urine flow rate and creatinine clearance by day 5 (168% and 147% compared to the baseline). CsA treatment alone significantly reduced urine flow rate and creatinine clearance on both day 5 and day 10 compared to baseline by 30–35% ($p<0.05$). The urine flow rate and creatinine clearance in animals treated with both CsA and rhRlx at either a dose of 0.1 mg/kg or 0.5 mg/kg were significantly improved compared to those of animals treated with CsA alone.

TABLE 11

Urine Flow

| Treatment Groups | Day 5 | Day 10 |
|---|---|---|
| Normal | 1.0 | 1.0 |
| Normal + 0.5 mg/kg rlx | 1.68 ± 0.02* | 1.42 ± 0.01* |
| CsA | 0.69 ± 0.04* | 0.85 ± 0.04* |
| CsA + 0.1 mg/kg rlx | 1.21 ± 0.36** | 1.59 ± 0.41** |
| CsA + 0.5 mg/kg rlx | 1.27 ± 0.16** | 1.067 ± 0.11** |

*$P < 0.05$ vs normal group
**$P < 0.05$ vs CsA group

TABLE 12

GFR

| Treatment Groups | Day 5 | Day 10 |
|---|---|---|
| Normal | 1.0 | 1.0 |
| Normal + 0.5 mg/kg rlx | 1.47 ± 0.08* | 1.50 ± 0.09* |
| CsA | 0.77 ± 0.07* | 0.8 ± 0.07* |
| CsA + 0.1 mg/kg rlx | 0.99 ± 0.15** | 1.49 ± 0.18** |
| CsA + 0.5 mg/kg rlx | 1.231 ± 0.15** | 1.39 ± 0.13** |

*$P < 0.05$ vs normal group
**$P < 0.05$ vs CsA group

The data indicate that relaxin significantly improves kidney function in CsA-treated animals.

Example 9

Relaxin Decreases Blood Pressure and Improves Kidney Function in Humans

A clinical trial was conducted with human subjects, age 18 to 70 years. Subjects were treated with either 10 μg relaxin/kg body weight/day (minimum of 36 subjects), 25 μg relaxin/kg body weight/day (minimum of 72 subjects), or placebo (minimum of 72 subjects) for 24 weeks. Administration was by continuous subcutaneous infusion, using a pump. The relaxin was recombinant human relaxin (rhRlx). At various time points, diastolic blood pressure, systolic blood pressure, and creatinine clearance (as a measure of renal function) were measured. Creatinine clearance was calculated using the following formulas:

For females:

Creatinine clearance=((140−age)×weight (kg)/72×serum creatinine (mg/dL))×0.85

For males:

Creatinine clearance=(140−age)×weight (kg)/72×serum creatinine (mg/dL)

The change in each measured parameter was calculated (value at week x−week 0 value). The results are shown in FIGS. 10–13. The results indicate that treatment with the 25 μg/kg/day dose of rhRLXN reduced diastolic and systolic pressure significantly from about week 2 through week 24. The threshold for obtaining this effect was greater than 10 μg rhRLXN/kg/day. The results further indicate that at both the 10 μg rhRLXN/kg/day and the 25 μg rhRLXN/kg/day treatments resulted in an improvement in renal function, as measured by an increase in creatinine clearance. This latter result indicates an increase in blood flow. Taken together, the data demonstrate that treatment with greater than 10 μg rhRLXN/kg body weight/day is effective in increasing cardiac output. The fact that a reduction in the cardiac afterload (as shown by the decrease in mean arterial pressure) without a worsening in renal function indicates that there was a concomitant increase in cardiac output as a result of the treatment.

Example 10

Relaxin Reduces Myogenic Reactivity of Isolated, Small Renal Arteries

Figure 14:
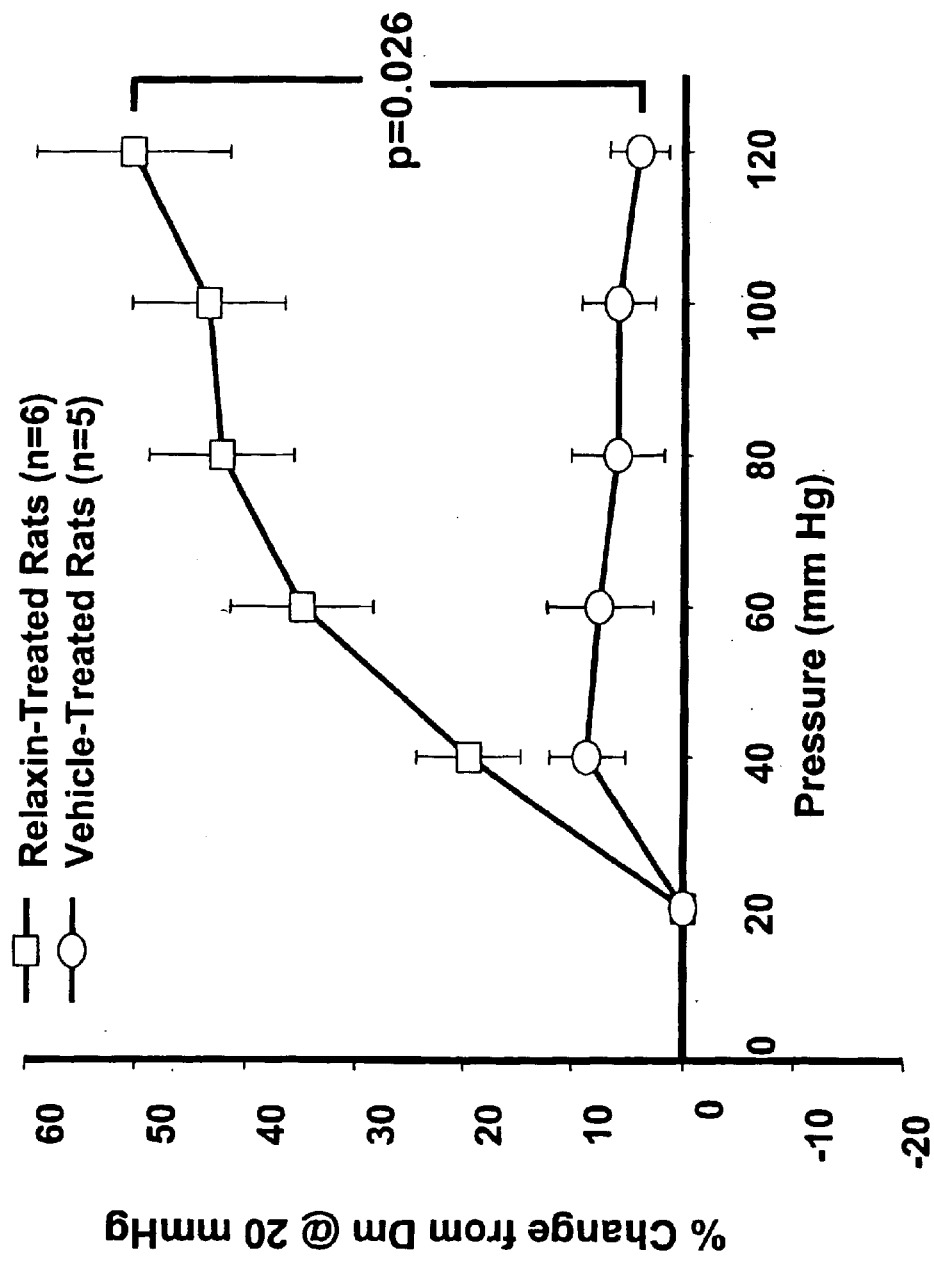
FIG. 14 is a graph depicting myogenic reactivity of small renal arteres.
Figure 15:
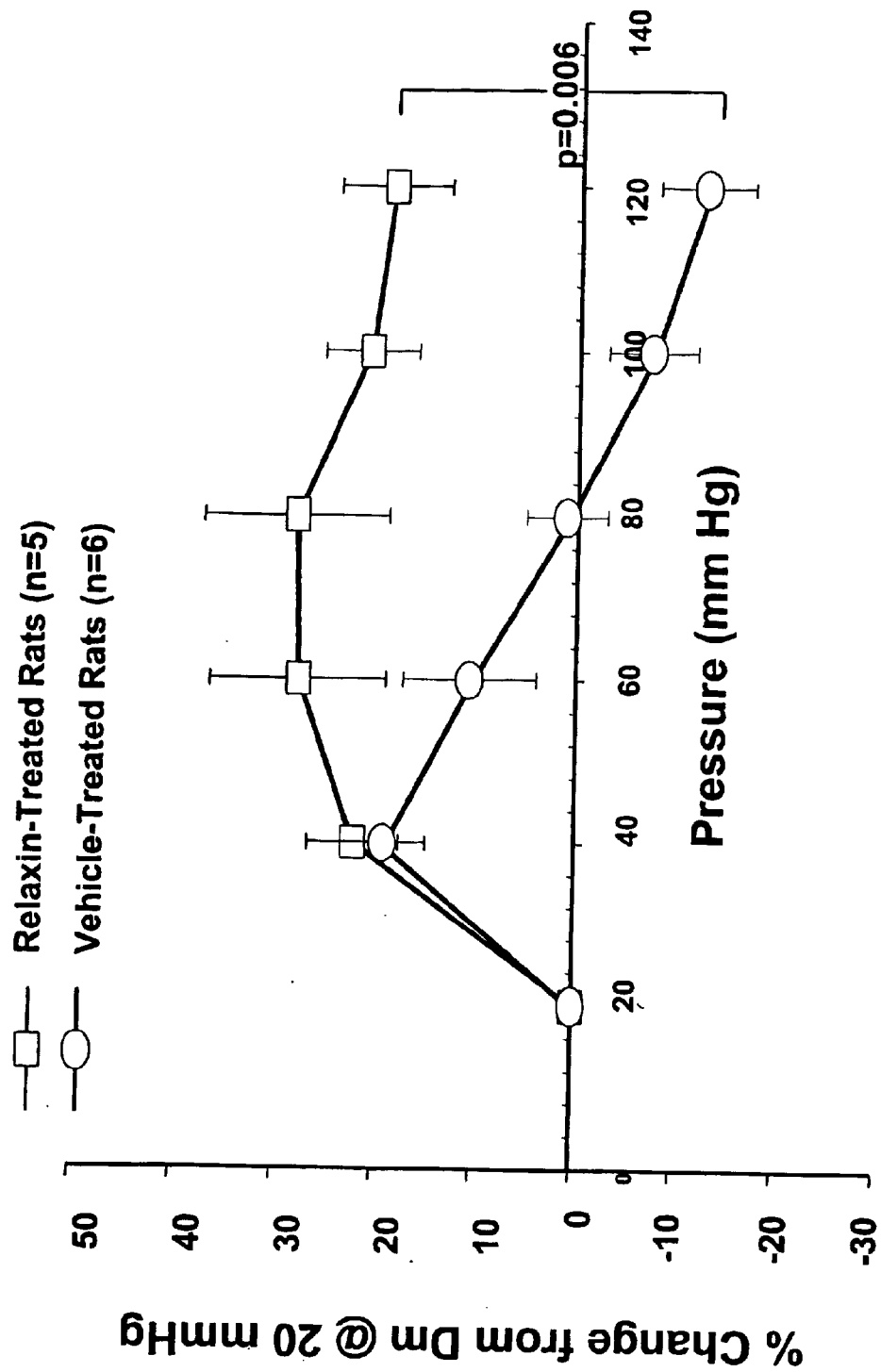
FIG. 15 is a graph depicting myogenic reactivity of small mesenteric arteries.

Myogenic reactivity is a dynamic and complex integrative vascular behavior which can be assessed in small renal arteries utilizing the pressurized arteriograph. Equivalent tone was first established in all vessels by constricting them to 75% of their baseline diameter at 60 mm Hg using the adrenergic agonist, phenylephrine. Next the arteries which began at an initial pressure of 20 mm Hg were subjected to a rapid increase in transmural pressure of 20 mm Hg increments in the absence of flow. FIG. 14 shows that when female rats are administered rhRLX for 5 days, small renal arteries isolated from these animals show reduced myogenic reactivity ex vivo. Vessels isolated from relaxin-treated rats showed a larger increase in diameter from baseline compared to those isolated from vehicle treated rats. These data demonstrate that rhRLX treatment in vivo decreases the vasoconstriction of renal vessels to rapid increases in pressure. This blunted myogenic reactivity following rhRLX treatment of nonpregnant rats mimics pregnancy (Gandley RE, Conrad KP, McLaughlin MK. Am J Physiol Integrative Comp Physiol 280:R1–R7, 2001). Morever, as during pregnancy, this blunted myogenic reactivity can be reversed by adding inhibitors of nitric oxide to the vessel bath. Furthermore, FIG. 15 shows that female rats chronically administered rhRLX also demonstrate reduced myogenic reactivity of small mesenteric arteries. That is, the effect of rhRLX does not apply only to the renal vasculature.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating hypertension, comprising administering to a patient in need thereof a pharmaceutical formulation comprising pharmaceutically active relaxin in an amount effective to reduce hypertension.

2. The method according to claim 1, wherein the hypertension is renal hypertension.

3. The method according to claim 1, wherein the hypertension is pulmonary hypertension.

4. The method of claim 1, wherein the relaxin is administered to the patient in an amount in a range of from 0.1 to 500 μg/kg of patient body weight.

5. The method of claim 1, wherein the formulation is administered daily over a period of time to reduce the hypertension in the patient.

6. The method of claim 1, wherein the formulation is an injectable formulation.

7. The method of claim 1, wherein relaxin is administered to the patient at a predetermined rate so as to maintain a serum concentration of relaxin of from 0.5 to 50 ng/ml and continuing the administration over a period of time to reduce the hypertension in the patient.

8. A method of treating hypertension, comprising administering an injectable formulation comprising pharmaceutically active recombinant human relaxin to a patient in an amount in a range of from 0.1 to 500 μg/kg of patient body weight, and continuing the administration over a period of time to reduce hypertension in the patient.

9. A method of increasing renal function, comprising administering to a patient in need thereof a pharmaceutical formulation comprising pharmaceutically active relaxin in an amount effective to increase a factor associated with renal function.

10. The method of claim 9, wherein the factor associated with renal function is glomerular filtration rate.

11. The method of claim 9, wherein the relaxin is administered to the patient in an amount in a range of from 0.1 to 500 μg/kg of patient body weight.

12. The method of claim 9, wherein the formulation is an injectable formulation, wherein the pharmaceutically active recombinant human relaxin is administered to a patient in an amount in a range of from 0.1 to 500 μg/kg of patient body weight, and wherein the administration is continued over a period of time to increase renal function in the patient.

13. A method of treating pulmonary hypertension, comprising administering to a patient in need thereof a pharmaceutical formulation comprising pharmaceutically active relaxin in an amount effective to reduce pulmonary hypertension.

14. The method of claim 13, wherein the relaxin is administered to the patient in an amount in a range of from 0.1 to 500 μg/kg of patient body weight.

15. The method of claim 13, wherein the formulation is administered daily over a period of time to reduce pulmonary hypertension in the patient.

16. The method of claim 13, wherein the formulation is an injectable formulation.

17. The method of claim 13, wherein relax in is administered to the patient at a predetermined rate so as to maintain a serum concentration of relaxin of from 0.5 to 50 ng/ml and continuing the administration over a period of time sufficient to reduce pulmonary hypertension in the patient.

* * * * *

UNITED STATES PATENT AND TRADEMARK OFFICE
CERTIFICATE OF CORRECTION

PATENT NO.    : 6,723,702 B2 Page 1 of 1
DATED         : April 20, 2004
INVENTOR(S)   : Conrad, Kirk P. et al.

It is certified that error appears in the above-identified patent and that said Letters Patent is hereby corrected as shown below:

Title page,
Item [73], Assignee, please delete "Ras Medical, Inc." and substitute therefore -- BAS Medical, Inc. --

Signed and Sealed this

Fifteenth Day of February, 2005

JON W. DUDAS
*Director of the United States Patent and Trademark Office*

SEQUENCE LISTING

<160> NUMBER OF SEQ ID NOS: 26

<210> SEQ ID NO 1
<211> LENGTH: 23
<212> TYPE: DNA
<213> ORGANISM: Rattus norvegicus

<400> SEQUENCE: 1
ttgcaaggcg aggcagcttg agt                                              23

<210> SEQ ID NO 2
<211> LENGTH: 22
<212> TYPE: DNA
<213> ORGANISM: Rattus norvegicus

<400> SEQUENCE: 2
ttcctgcaaa aacacagact cg                                               22

<210> SEQ ID NO 3
<211> LENGTH: 22
<212> TYPE: DNA
<213> ORGANISM: Rattus norvegicus

<400> SEQUENCE: 3
ggtctttccg gtgagaggtc ta                                               22

<210> SEQ ID NO 4
<211> LENGTH: 21
<212> TYPE: DNA
<213> ORGANISM: Rattus norvegicus

<400> SEQUENCE: 4
ccagaaaaat gtgacaagcc a                                                21

<210> SEQ ID NO 5
<211> LENGTH: 22
<212> TYPE: DNA
<213> ORGANISM: Rattus norvegicus

<400> SEQUENCE: 5
gcagatgtga atgcagacca aa                                               22

<210> SEQ ID NO 6
<211> LENGTH: 21
<212> TYPE: DNA
<213> ORGANISM: Rattus norvegicus

<400> SEQUENCE: 6
ctagttcccg aaaccctgag g                                                21

<210> SEQ ID NO 7
<211> LENGTH: 25
<212> TYPE: DNA
<213> ORGANISM: Rattus norvegicus

<400> SEQUENCE: 7
tgtccatcaa gggagtgtgt gcgaa                                            25

<210> SEQ ID NO 8
<211> LENGTH: 24
<212> TYPE: DNA
<213> ORGANISM: Rattus norvegicus

```
<400> SEQUENCE: 8
ctacagctcc aagcagaaga gaga                                              24

<210> SEQ ID NO 9
<211> LENGTH: 22
<212> TYPE: DNA
<213> ORGANISM: Rattus norvegicus

<400> SEQUENCE: 9
agttattgga ctccaggcgt tc                                                22

<210> SEQ ID NO 10
<211> LENGTH: 24
<212> TYPE: DNA
<213> ORGANISM: Rattus norvegicus

<400> SEQUENCE: 10
acccatcacc atcttccagg agcg                                              24

<210> SEQ ID NO 11
<211> LENGTH: 20
<212> TYPE: DNA
<213> ORGANISM: Rattus norvegicus

<400> SEQUENCE: 11
ttcaatggca cagtcaaggc                                                   20

<210> SEQ ID NO 12
<211> LENGTH: 21
<212> TYPE: DNA
<213> ORGANISM: Rattus norvegicus

<400> SEQUENCE: 12
tcaccccatt tgatgttagc g                                                 21

<210> SEQ ID NO 13
<211> LENGTH: 27
<212> TYPE: DNA
<213> ORGANISM: Homo sapiens

<400> SEQUENCE: 13
agcaagacaa gaaaatccct gtgggcc                                           27

<210> SEQ ID NO 14
<211> LENGTH: 22
<212> TYPE: DNA
<213> ORGANISM: Homo sapiens

<400> SEQUENCE: 14
ccagcacata ggagagatga gc                                                22

<210> SEQ ID NO 15
<211> LENGTH: 21
<212> TYPE: DNA
<213> ORGANISM: Homo sapiens

<400> SEQUENCE: 15
ggaacattta cacgtctgcg g                                                 21

<210> SEQ ID NO 16
<211> LENGTH: 25
<212> TYPE: DNA
```

<210> SEQ ID NO 16
<211> LENGTH: 25
<212> TYPE: DNA
<213> ORGANISM: Homo sapiens

<400> SEQUENCE: 16
agaaaaatgt gacaagccga ggcgg                                 25

<210> SEQ ID NO 17
<211> LENGTH: 22
<212> TYPE: DNA
<213> ORGANISM: Homo sapiens

<400> SEQUENCE: 17
ccactgagga gtccaacatc ac                                    22

<210> SEQ ID NO 18
<211> LENGTH: 21
<212> TYPE: DNA
<213> ORGANISM: Homo sapiens

<400> SEQUENCE: 18
agatctggtt cccgaaaccc t                                     21

<210> SEQ ID NO 19
<211> LENGTH: 25
<212> TYPE: DNA
<213> ORGANISM: Homo sapiens

<400> SEQUENCE: 19
tatgtggcac tgaaacgaac tgggc                                 25

<210> SEQ ID NO 20
<211> LENGTH: 24
<212> TYPE: DNA
<213> ORGANISM: Homo sapiens

<400> SEQUENCE: 20
gaaggaagat ggaagattac tggc                                  24

<210> SEQ ID NO 21
<211> LENGTH: 20
<212> TYPE: DNA
<213> ORGANISM: Homo sapiens

<400> SEQUENCE: 21
ttctgcccag gtcctgtttt                                       20

<210> SEQ ID NO 22
<211> LENGTH: 24
<212> TYPE: DNA
<213> ORGANISM: Homo sapiens

<400> SEQUENCE: 22
tggacttcca ttcacttgca aggc                                  24

<210> SEQ ID NO 23
<211> LENGTH: 24
<212> TYPE: DNA
<213> ORGANISM: Homo sapiens

<400> SEQUENCE: 23
tgtaggtctt taccccgata gctc                                  24

<210> SEQ ID NO 24
<211> LENGTH: 20

```
-continued

<212> TYPE: DNA
<213> ORGANISM: Homo sapiens

<400> SEQUENCE: 24
caagcttccc gttctcagcc                                              20

<210> SEQ ID NO 25
<211> LENGTH: 19
<212> TYPE: DNA
<213> ORGANISM: Homo sapiens

<400> SEQUENCE: 25
gaaggtgaag gtcggagtc                                               19

<210> SEQ ID NO 26
<211> LENGTH: 20
<212> TYPE: DNA
<213> ORGANISM: Homo sapiens

<400> SEQUENCE: 26
gaagatggtg atgggatttc                                              20
```